(12) United States Patent
Wang et al.

(10) Patent No.: US 12,116,348 B2
(45) Date of Patent: Oct. 15, 2024

(54) SUBSTITUTED BENZIMIDAZOLE COMPOUND AND COMPOSITION COMPRISING SAME

(71) Applicant: Shenzhen TargetRx, Inc., Guangdong (CN)

(72) Inventors: Yihan Wang, Guangdong (CN); Zhiqiang Liu, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 1190 days.

(21) Appl. No.: 16/964,257

(22) PCT Filed: Nov. 13, 2018

(86) PCT No.: PCT/CN2018/115161
§ 371 (c)(1),
(2) Date: Jul. 23, 2020

(87) PCT Pub. No.: WO2019/096112
PCT Pub. Date: May 23, 2019

(65) Prior Publication Data
US 2023/0192625 A1 Jun. 22, 2023

(30) Foreign Application Priority Data

Nov. 14, 2017 (CN) ............ 201711118845.0

(51) Int. Cl.
*A61P 35/00* (2006.01)
*C07D 235/06* (2006.01)

(52) U.S. Cl.
CPC ............ *C07D 235/06* (2013.01); *A61P 35/00* (2018.01); *C07B 2200/05* (2013.01)

(58) Field of Classification Search
CPC .................................................. A61P 35/00
See application file for complete search history.

(56) References Cited

U.S. PATENT DOCUMENTS

| | | | |
|---|---|---|---|
| 7,842,816 B2 | 11/2010 | Wallace et al. | |
| 8,193,231 B2 | 6/2012 | Wallace et al. | |
| 8,198,305 B2 | 6/2012 | Harbeson | |
| 9,156,795 B2 | 10/2015 | DeMattei et al. | |
| 9,382,212 B1 | 7/2016 | Krell et al. | |
| 2006/0106225 A1 | 5/2006 | Wallace et al. | |

FOREIGN PATENT DOCUMENTS

| | | |
|---|---|---|
| CN | 1652776 A | 8/2005 |
| CN | 1652792 A | 8/2005 |
| CN | 1874768 A | 12/2006 |
| CN | 101360718 A | 2/2009 |
| CN | 103764134 A | 4/2014 |
| CN | 104870427 A | 8/2015 |
| WO | WO 95/26325 A2 | 10/1995 |
| WO | WO 2003/077914 A2 | 9/2003 |
| WO | WO 2007/076245 A1 | 7/2007 |

OTHER PUBLICATIONS

International Search Report and Written Opinion for Application No. PCT/CN2018/115161, mailed Jan. 30, 2019.
Chinese Office Action for Application No. 201811344212.6, mailed Dec. 12, 2019.
Harbeson et al., Chapter 24—Deuterium in Drug Discovery and Development. Annual Reports in Medicinal Chemistry. 2011; 46: 403-417.
Shao et al., Derivatives of tramadol for increased duration of effect. Bioorg Med Chem Lett. Feb. 2006;16(3):691-4. doi: 10.1016/j.bmcl. 2005.10.024. Epub Oct. 27, 2005.
Declaration under 37 CFR § 1.132 for Vinita Uttamsingh, dated Feb. 1, 2012, with Attachment B. 5 pages.
PCT/CN2018/115161, Jan. 30, 2019, International Search Report and Written Opinion and English Translation Thereof.
CN201811344212.6, Dec. 12, 2019, Chinese Office Action and English Translation Thereof.
EP18879844.1, Apr. 12, 2021, Extended European Search Report.
Extended European Search Report for Application No. 18879844.1, mailed Apr. 12, 2021.
Tung, The development of deuterium-containing drugs. Innovations in Pharmaceutical Technology. Mar. 1, 2010; 32(32):24-28.

*Primary Examiner* — Genevieve S Alley
(74) *Attorney, Agent, or Firm* — Wolf, Greenfield & Sacks, P.C.

(57) ABSTRACT

Provided are a substituted benzimidazole compound, and a composition comprising same and use thereof. The substituted benzimidazole compound is a compound represented by formula (I), or a pharmaceutically acceptable salt, prodrug, hydrate or solvate compound, polymorph, stereoisomer, or isotopic variation thereof. The compound can be used for treating and/or preventing related diseases caused by MEK, such as hyperproliferative diseases, pancreatitis, kidney diseases, blastocyte implantation, and diseases related to vasculogenesis or angiogenesis.

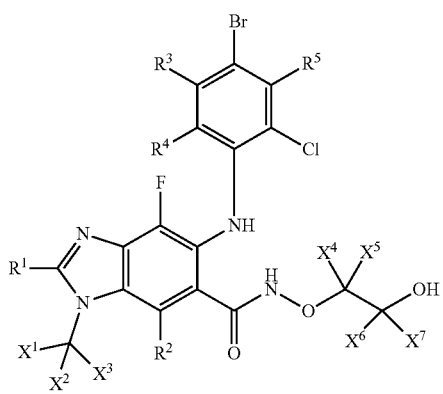

Formula (I)

16 Claims, No Drawings

SUBSTITUTED BENZIMIDAZOLE COMPOUND AND COMPOSITION COMPRISING SAME

CROSS REFERENCE TO RELATED APPLICATIONS

The present application is a national application of PCT/CN2018/115161 filed on Nov. 13, 2018, which claims the priority of the Chinese Patent Application No. 201711118845.0 filed on Nov. 14, 2017. The Chinese Patent Application No. 201711118845.0 is incorporated herein by reference as part of the disclosure of the present application.

FIELD OF THE INVENTION

The present disclosure relates to the field of pharmaceutical technology, particularly relates to a substituted benzimidazole compound, a composition comprising the same and use thereof. More specifically, the present disclosure relates to some deuterated 6-(4-bromo-2-chloro-phenylamino)-7-fluoro-3-(methyl)-3H-benzimidazole-5-carboxylic acid (2-hydroxyethoxy)-amide compounds. These deuterated compounds have inhibitory activities against MEK protein tyrosine kinase, and can be used in the treatment and/or prevention of diseases caused by MEK kinase, with better pharmacokinetic properties.

BACKGROUND OF THE INVENTION

Mitogen-activated protein kinases (MAPK) are a class of serine/threonine protein kinases in cells. Studies have demonstrated that MAPK signal transduction pathways exist in most cells, which play a vital role in the process of transducing the extracellular stimulation signals into cells and nuclei thereof, and causing biological responses in cells. MAPK have three parallel signaling pathways: 1) ERK signaling pathway (External-signal regulated kinase, MAPK/ERK); 2) JNK/SAPK signaling pathway; and 3) P38MAPK pathway.

The MAPK/ERK signaling pathway is a key pathway for the transmission of extracellular signals into cells, and it is also an attractive research object in the past decade to study the signaling pathways of cell proliferation, differentiation and apoptosis. The specific pathway is RAS-RAF-MEK-MAPK/ERK. When an extracellular stimulus (such as a growth factor) binds to the corresponding receptor, growth factor receptor-bound protein 2 (Grb2) binds to the activated receptor, and then interacts with the proline-enriched sequence at the C-terminus of the guanine nucleotide exchange factor (GEF) SOS to form a receptor-Grb2-SOS complex. The SOS binds to the tyrosine (Tyr) phosphorylation site on the receptor or the receptor substrate, resulting in the translocation of the cytoplasmic protein SOS to membrane, and forming a high concentration of SOS near Ras. The SOS binds to RAS-GDP, which promotes GTP to replace the GDP on Ras, and thus activating Ras. The activated Ras binds to Raf as an adaptor protein and transfers Raf from cytoplasm to cell membrane. After being activated by Raf kinase, the catalytic domain at C-terminus of Raf may bind to MEK, and phosphorylate the Thr and Ser in the catalytic domain of MEK, thereby activating MEK. MEK may phosphorylate and activate the TXY motif in the catalytic domain of ERK. ERK is the core element downstream of the Ras mitogen signal transduction. Activated ERK may promote the phosphorylation of cytoplasmic target proteins or regulate the activity of other protein kinases. More importantly, the activated ERK may enter the nucleus and promote the phosphorylation of various transcription factors.

MEK is the only substrate of RAF. ERK is the only substrate of MEK, and ERK can only be activated by MEK. Because of the above specificity, MEK plays a very important role in the RAS-RAF-MEK-MAPK/ERK signaling pathway, which has also become a more attractive target of the anti-proliferative drugs for current researches.

Selumetinib, also known as AZD6244, with a chemical name of 6-(4-bromo-2-chloro-phenylamino)-7-fluoro-3-methyl-3H-benzimidazole-5-carboxylic acid (2-hydroxyethoxy)-amide, is a MEK inhibitor developed by Array BioPharma and later transferred to AstraZeneca. At present, the research of Selumetinib in the treatment of various cancers, such as non-small cell lung cancer, breast cancer, thyroid cancer, etc., is in the clinical stage.

Therefore, it is still necessary to develop compounds that are suitable being used as MEK inhibitors with selective inhibitory activity or better pharmacodynamics/pharmacokinetics in this field. The present disclosure provides a novel MEK inhibitor, obtained by deuterating Selumetinib as the parent compound. Through the deuteration strategy of the present disclosure, the undesired metabolites are reduced or eliminated; the half-life of the parent compound is increased; the number of doses required to achieve the desired effects is reduced; the formation of active metabolites (if any) is increased; the production of harmful metabolites in the specific tissues is reduced; and more effective and/or safer drugs for the multiple medication (regardless of whether it is intended) is produced.

SUMMARY OF THE INVENTION

In view of the above technical problems, the present disclosure provides a novel substituted benzimidazole compound, a composition comprising the same and use thereof, wherein the compounds can be used in the treatment of hyperproliferative diseases. Specifically, the present disclosure relates to a compound of formula (I) used as a MEK inhibitor. The present disclosure also provides a method of treating cancers.

In this regard, the technical solutions adopted by the present disclosure are as follows:

In the first aspect, the present disclosure provides a compound of formula (I):

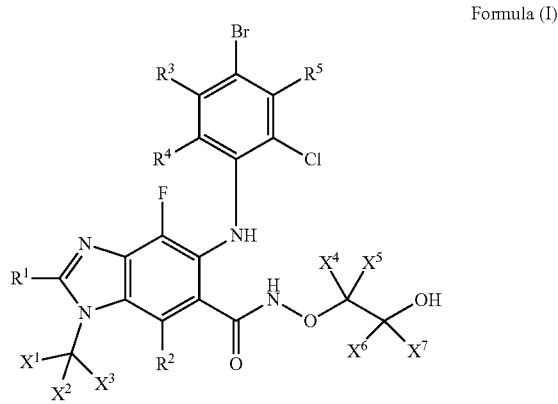

Formula (I)

wherein, $R^1$, $R^2$, $R^3$, $R^4$, $R^5$, $X^1$, $X^2$, $X^3$, $X^4$, $X^5$, $X^6$ and $X^7$ are independently selected from hydrogen or deuterium;

with the proviso that at least one of $R^1$, $R^2$, $R^3$, $R^4$, $R^5$, $X^1$, $X^2$, $X^3$, $X^4$, $X^5$, $X^6$ and $X^7$ is deuterated or deuterium;

or a pharmaceutically acceptable salt, prodrug, hydrate, solvate, polymorph, stereoisomer or isotopic variant thereof.

In another aspect, the present disclosure provides a pharmaceutical composition, which comprises the compound of the present disclosure and pharmaceutically acceptable excipient(s). In a specific embodiment, the compound of the present disclosure is provided in an effective amount in the pharmaceutical composition. In a specific embodiment, the compound of the present disclosure is provided in a therapeutically effective amount. In a specific embodiment, the compound of the present disclosure is provided in a prophylactically effective amount.

In another aspect, the present disclosure provides a method of preparing the pharmaceutical composition described above, comprising the steps of: mixing the pharmaceutically acceptable excipient(s) with the compound of the present disclosure, thereby forming the pharmaceutical composition.

In another aspect, the present disclosure provides a method of treating and/or preventing the disease caused by MEK in a subject in need thereof. The method comprises administering to the subject an effective amount of the compound disclosed herein. In a specific embodiment, the disease caused by MEK is selected from: hyperproliferative disease, pancreatitis, renal disease, embryonic cell transplantation, disease related to vasculogenesis or angiogenesis. In a specific embodiment, the hyperproliferative disease is selected from cancer, such as brain cancer, lung cancer, squamous cell carcinoma, bladder cancer, gastric cancer, pancreatic cancer, breast cancer, head and neck cancer, kidney cancer, ovarian cancer, prostate cancer, colorectal cancer, esophageal cancer, testicular cancer, thyroid cancer, and the like. In a specific embodiment, the compound is administered orally, subcutaneously, intravenously or intramuscularly. In a specific embodiment, the compound is administered chronically.

DETAILED DESCRIPTION OF THE INVENTION

Compared with the non-deuterated compound, the deuterated MEK inhibitor compounds and the pharmaceutically acceptable salts thereof have better pharmacokinetic and/or pharmacodynamic properties. Therefore, they are more suitable compounds as MEK inhibitors, and more suitable for the preparation of the medicament for the treatment of MEK-mediated diseases. On this basis, the present disclosure is completed.

Definitions

As used herein, unless otherwise specified, "deuterated" means that one or more hydrogens in a compound or group are substituted by deuterium; the "deuterated" may be mono-substituted, di-substituted, poly-substituted or fully-substituted by deuterium. The terms "substituted with one or more deuteriums" and "substituted one or more times by deuterium" are used interchangeably.

As used herein, unless otherwise specified, "non-deuterated compound" refers to a compound wherein the content of the deuterium atom is not higher than the natural content of the deuterium isotope (0.015%).

Also disclosed herein are isotopically labeled compounds to the extent of the original compounds disclosed herein. Examples of isotopes that can be listed in compounds disclosed herein include hydrogen, carbon, nitrogen, oxygen, phosphorus, sulfur, fluorine and chlorine isotopes, such as $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. A compound disclosed herein containing the above isotope or other isotopic atoms, or an enantiomer, a diastereomer, an isomer, or a pharmaceutically acceptable salt or a solvate thereof are all within the scope disclosed herein. Certain isotopically labeled compounds disclosed herein, such as the radioisotopes of $^3H$ and $^{14}C$, are also among them and are useful in the tissue distribution experiments of drugs and substrates. Tritium, i.e., $^3H$, and carbon-14, i.e., $^{14}Cl$, are easier to be prepared and detected and are the first choice for isotopes. Isotopically-labeled compounds can be prepared using the schemes shown in the Examples by conventional methods by replacing the non-isotopic reagents with readily available isotopically labeled reagents.

The compound disclosed herein may include one or more asymmetric centers, and thus may exist in a variety of "stereoisomeric" forms, for example, enantiomeric and/or diastereomeric forms. For example, the compound disclosed herein may be in the form of an individual enantiomer, a diastereomer or a geometric isomer (e.g., cis- and trans-isomers), or may be in the form of a mixture of stereoisomers, including a racemic mixture and a mixture enriched in one or more stereoisomers. The isomers can be separated from the mixture by methods known to those skilled in the art, including: chiral high pressure liquid chromatography (HPLC) and formation and crystallization of a chiral salt; or preferred isomers can be prepared by asymmetric synthesis.

As used herein, the term "compound of the present disclosure" (or "compound disclosed herein") refers to the compounds represented by formula (I). The term also includes pharmaceutically acceptable salts, prodrugs, hydrates, solvates, polymorphs, stereoisomers or isotopic variants of the compounds of formula (I).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19.

Pharmaceutically acceptable salts of the compounds disclosed herein include those derived from suitable inorganic and organic acids and inorganic and organic bases. Examples of pharmaceutically acceptable, nontoxic acid addition salts are salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Also included are salts formed by using conventional methods in the art, such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium salts, and the like. If appropriate, other pharmaceutically acceptable salts include, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to a complex in which a compound disclosed herein coordinates with a solvent molecule in a particular ratio. "Hydrate" refers to a complex formed by coordination of a compound disclosed herein with water.

The term "prodrug" includes a class of compounds which may themselves be biologically active or inactive, and when taken by a suitable method, are converted into a compound of formula (I), or a salt or a solution of a compound of formula (I) by metabolism or chemical reaction in the human body. The prodrug includes, but is not limited to, the compounds in which an amino acid residue or a polypeptide chain consisting of one or more (e.g., 2, 3 or 4) amino acid residues is covalently linked by an amide or ester linkage on the free amino, hydroxyl or carboxyl group of the compound disclosed herein. The amino acid residue includes, but is not limited to, not only 20 natural amino acids usually represented by 3 letter symbols, but also 4-hydroxyproline, hydroxyl lysine, Demosine, isodemosine, 3-methylhistidine, norvaline, ornithine and methionine sulfone. Other types of prodrugs are also included. For example, a free carboxyl group can be derivatized as an amide or an alkyl ester. As described in Advanced Drug Delivery Reviews 1996, 19, 115, free hydroxyl groups are derivatized by the use of groups including, but not limited to, hemisuccinates, phosphates, dimethylaminoacetates, and phosphoryloxymethoxy carbonyl groups. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphoramides. All of these other moieties may incorporate groups including but not limited to ether, amine and carboxylic acid functionalities.

The term "polymorph" refers to a different manner in which the molecules of a chemical drug are arranged, and is generally expressed as the form in which the pharmaceutical material is present in a solid state. One drug may exist in a plurality of crystalline forms. Different crystalline forms of the same drug may have different dissolution and absorption in the body, thereby affecting the dissolution and release of the formulation.

As used herein, the term "subject" includes, but is not limited to, humans (i.e., a male or female of any age group, e.g., a pediatric subject (e.g, infant, child, adolescent) or adult subject (e.g., young adult, middle-aged adult or elderly adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

"Disease", "disorder" and "condition" are used interchangeably herein.

As used herein, and unless otherwise specified, the terms "treat", "treating", and "treatment" contemplate an action that occurs while a subject is suffering from a particular disease, disorder, or condition, which reduces the severity of the disease, disorder or condition, or retards or slows the progression of the disease, disorder or condition ("therapeutic treatment"). The term also contemplates an action that occurs before a subject begins to suffer from a specific disease, disorder or condition ("prophylactic treatment").

In general, the "effective amount" of a compound refers to an amount sufficient to elicit the desired biological response. As will be appreciated by those of ordinary skill in this art, the effective amount of a compound disclosed herein may vary depending on such factors as the desired biological endpoint, the pharmacokinetics of the compound, the disease being treated, the mode of administration, and the age, health, and condition of the subject. An effective amount encompasses therapeutically and prophylactically effective amount.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

"Combination" and related terms mean the simultaneous or sequential administration of a compound of the present disclosure. For example, a compound disclosed herein may be administered simultaneously or sequentially with another therapeutic agent in separate unit dosage forms, or together with another therapeutic agent in a single unit dosage form.

Compounds

The present disclosure provides a benzimidazole compound of formula (I), or a pharmaceutically acceptable salt, prodrug, hydrate, solvate, polymorph, stereoisomer or isotopic variant thereof:

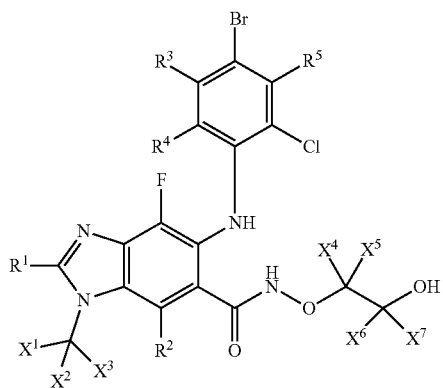

Formula (I)

wherein, $R^1$, $R^2$, $R^3$, $R^4$, $R^5$, $X^1$, $X^2$, $X^3$, $X^4$, $X^5$, $X^6$ and $X^7$ are independently selected from hydrogen or deuterium;

with the proviso that at least one of $R^1$, $R^2$, $R^3$, $R^4$, $R^5$, $X^1$, $X^2$, $X^3$, $X^4$, $X^5$, $X^6$ and $X^7$ is deuterated or deuterium.

As an alternative embodiment of the present disclosure, the compound of formula (I) contains at least one deuterium atom, alternatively one deuterium atom, alternatively two deuterium atoms, alternatively three deuterium atoms, alternatively four deuterium atoms, alternatively five deuterium atoms, alternatively six deuterium atoms, alternatively seven deuterium atoms, alternatively eight deuterium atoms, and alternatively nine deuterium atoms.

As an alternative embodiment of the present disclosure, the content of deuterium isotope in each deuterated position is at least greater than the natural content of deuterium isotope (0.015%), alternatively greater than 30%, alternatively greater than 50%, alternatively greater than 75%, alternatively greater than 95%, and alternatively greater than 99%.

Specifically, in the present disclosure, the content of the deuterium isotope in each deuterated position of $R^1$, $R^2$, $R^3$, $R^4$, $R^5$, $X^1$, $X^2$, $X^3$, $X^4$, $X^5$, $X^6$ and $X^7$ is at least 5%, alternatively greater than 10%, alternatively greater than 15%, alternatively greater than 20%, alternatively greater than 25%, alternatively greater than 30%, alternatively greater than 35%, alternatively greater than 40%, alternatively greater than 45%, alternatively greater than 50%, alternatively greater than 55%, alternatively greater than 60%, alternatively greater than 65%, alternatively greater than 70%, alternatively greater than 75%, alternatively greater than 80%, alternatively greater than 85%, alternatively greater than 90%, alternatively greater than 95%, and alternatively greater than 99%.

In another specific embodiment, among $R^1$, $R^2$, $R^3$, $R^4$, $R^5$, $X^1$, $X^2$, $X^3$, $X^4$, $X^5$, $X^6$ and $X^7$ of the compound of formula (I), at least one of them contains deuterium, alternatively two contain deuterium, alternatively three contain deuterium, alternatively four contain deuterium, alternatively five contain deuterium, alternatively six contain deuterium, alternatively seven contain deuterium, alternatively eight contain deuterium, alternatively nine contain deuterium, alternatively ten contain deuterium, alternatively eleven contain deuterium, and alternatively twelve contain deuterium. Specifically, the compound of formula (I) contains at least one, two, three, four, five, six, seven, eight, nine, ten, eleven or twelve deuterium atoms.

As an alternative embodiment of the present disclosure, $R^1$, $R^2$, $R^3$, $R^4$ and $R^5$ are independently selected from hydrogen or deuterium.

In another specific embodiment, $R^1$ is deuterium.
In another specific embodiment, $R^2$ is deuterium.
In another specific embodiment, $R^3$ is deuterium.
In another specific embodiment, $R^4$ is deuterium.
In another specific embodiment, $R^5$ is deuterium.

As an alternative embodiment of the present disclosure, $X^1$, $X^2$, $X^3$, $X^4$, $X^5$, $X^6$ and $X^7$ are independently selected from hydrogen or deuterium.

In another specific embodiment, $X^1$, $X^2$ and $X^3$ are the same; alternatively, $X^1$, $X^2$ and $X^3$ are deuterium; alternatively, $X^1$, $X^2$ and $X^3$ are hydrogen.

In another specific embodiment, $X^6$ and $X^7$ are the same. Alternatively, $X^6$ and $X^7$ are deuterium; alternatively, $X^6$ and $X^7$ are hydrogen.

In a specific embodiment, "$R^1$, $R^2$, $R^3$, $R^4$ and $R^5$ are independently selected from hydrogen or deuterium" includes the technical solutions wherein, $R^1$ is selected from hydrogen or deuterium, $R^2$ is selected from hydrogen or deuterium, $R^3$ is selected from hydrogen or deuterium and so on, until $R^5$ is selected from hydrogen or deuterium. More specifically, the technical solutions wherein, $R^1$ is hydrogen, $R^1$ is deuterium, $R^2$ is hydrogen, $R^2$ is deuterium, $R^3$ is hydrogen, $R^3$ is deuterium and so on, until $R^5$ is hydrogen, $R^5$ is deuterium, are included.

In a specific embodiment, "$X^1$, $X^2$, $X^3$, $X^4$, $X^5$, $X^6$ and $X^7$ are independently selected from hydrogen or deuterium" includes the technical solutions wherein, $X^1$ is selected from hydrogen or deuterium, $X^2$ is selected from hydrogen or deuterium, $X^3$ is selected from hydrogen or deuterium and so on, until $X^7$ is selected from hydrogen or deuterium. More specifically, the technical solutions wherein, X' is hydrogen, $X^1$ is deuterium, $X^2$ is hydrogen, $X^2$ is deuterium, $X^3$ is hydrogen, $X^3$ is deuterium and so on, until $X^7$ is hydrogen, $X^7$ is deuterium, are included.

As an alternative embodiment of the present disclosure, the present disclosure relates to a compound of formula (I), wherein $R^1$ to $R^3$ and $R^5$ are hydrogen, $R^4$, $X^1$ to $X^7$ are independently selected from hydrogen or deuterium, with the proviso that the compound contains at least one deuterium atom.

As an alternative embodiment of the present disclosure, the present disclosure relates to a compound of formula (I), wherein $R^1$ to $R^5$ are hydrogen, $X^1$ to $X^7$ are independently selected from hydrogen or deuterium, with the proviso that the compound contains at least one deuterium atom. As an alternative embodiment of the present disclosure, the present disclosure relates to a compound of formula (I), wherein $R^1$ to $R^3$, $R^5$, $X^4$ and $X^5$ are hydrogen, $R^4$, $X^1$ to $X^3$, $X^6$ and $X^7$ are independently selected from hydrogen or deuterium, with the proviso that the compound contains at least one deuterium atom.

As an alternative embodiment of the present disclosure, the present disclosure relates to a compound of formula (I), wherein $R^1$ to $R^5$, $X^4$ and $X^5$ are hydrogen, $X^1$ to $X^3$, $X^6$ and $X^7$ are independently selected from hydrogen or deuterium, with the proviso that the compound contains at least one deuterium atom.

As an alternative embodiment of the present disclosure, the present disclosure relates to a compound of formula (I), wherein $R^1$ to $R^3$, $R^5$, $X^6$ and $X^7$ are hydrogen, $R^4$, $X^1$ to $X^5$ are independently selected from hydrogen or deuterium, with the proviso that the compound contains at least one deuterium atom.

As an alternative embodiment of the present disclosure, the present disclosure relates to a compound of formula (I), wherein $R^1$ to $R^5$, $X^6$ and $X^7$ are hydrogen, $X^1$ to $X^5$ are independently selected from hydrogen or deuterium, with the proviso that the compound contains at least one deuterium atom.

As an alternative embodiment of the present disclosure, the present disclosure relates to a compound of formula (I), wherein $R^1$ to $R^3$, $R^5$ and $X^4$ to $X^7$ are hydrogen, $R^4$, $X^1$ to $X^3$ are independently selected from hydrogen or deuterium, with the proviso that the compound contains at least one deuterium atom.

As an alternative embodiment of the present disclosure, the present disclosure relates to a compound of formula (I), wherein $R^1$ to $R^5$ and $X^4$ to $X^7$ are hydrogen, $X^1$ to $X^3$ are independently selected from hydrogen or deuterium, with the proviso that the compound contains at least one deuterium atom.

As an alternative embodiment of the present disclosure, the present disclosure relates to a compound of formula (I), wherein $X^1$ to $X^3$ are deuterium, $R^1$ to $R^5$, $X^4$ to $X^7$ are independently selected from hydrogen or deuterium.

As an alternative embodiment of the present disclosure, the present disclosure relates to a compound of formula (I), wherein $R^1$ to $R^3$ and $R^5$ are hydrogen, $X^1$ to $X^3$ are deuterium, $R^4$, $X^4$ to $X^7$ are independently selected from hydrogen or deuterium.

As an alternative embodiment of the present disclosure, the present disclosure relates to a compound of formula (I), wherein $R^1$ to $R^5$ are hydrogen, $X^1$ to $X^3$ are deuterium, $X^4$ to $X^7$ are independently selected from hydrogen or deuterium.

As an alternative embodiment of the present disclosure, the compound is selected from the following group of compounds or the pharmaceutically acceptable salts thereof:

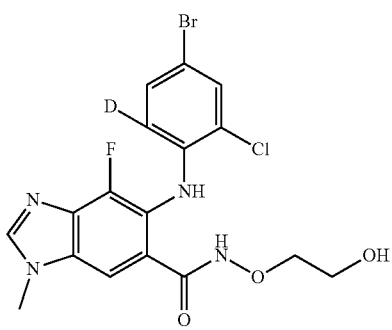

Formula (1)

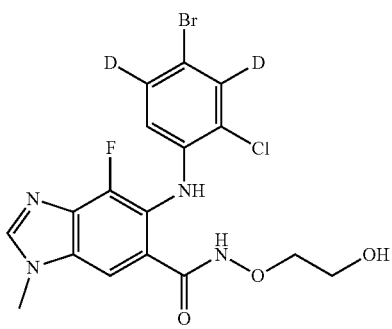

Formula (2)

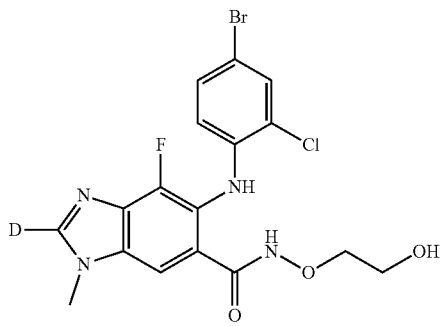

Formula (3)

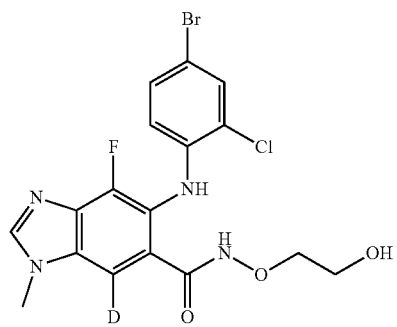

Formula (4)

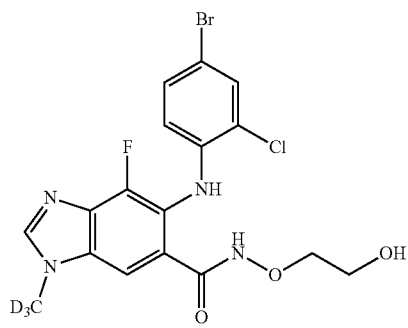

Formula (5)

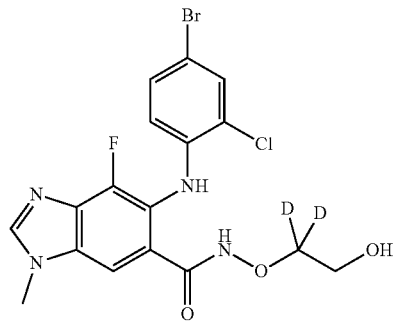

Formula (6)

-continued
Formula (7)
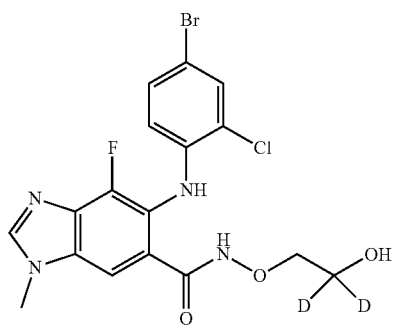
Formula (8)
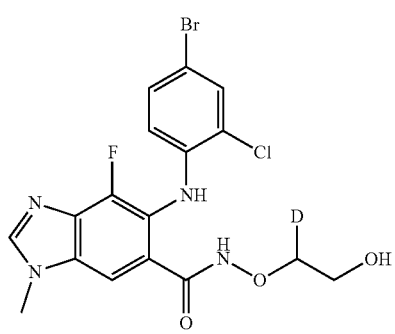
Formula (9)
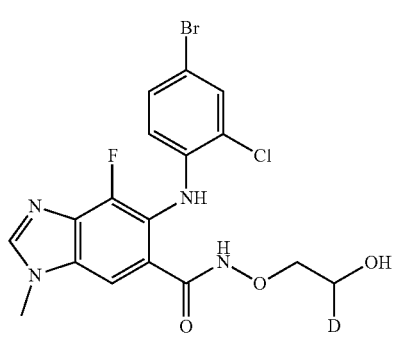
Formula (10)
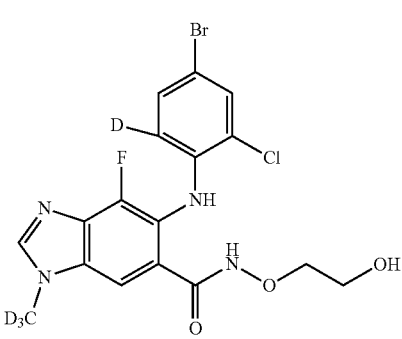
-continued
Formula (11)
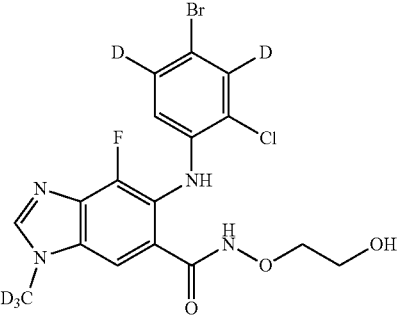
Formula (12)
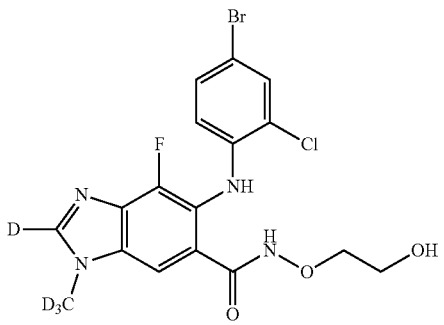
Formula (13)
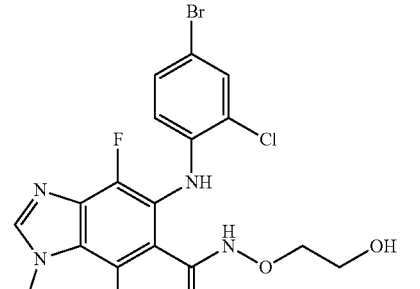
Formula (14)
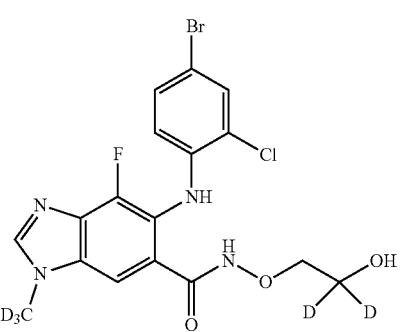
Formula (15)
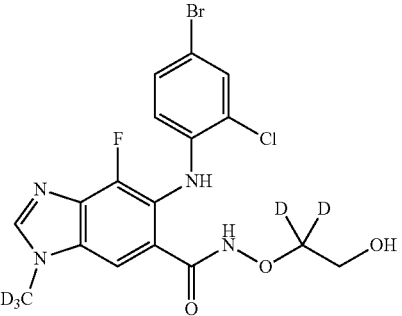

Formula (16)
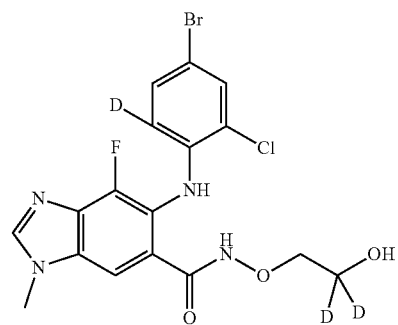
Formula (17)
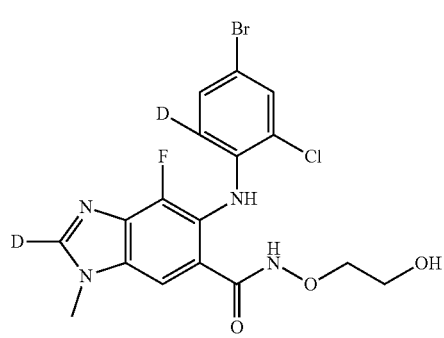
Formula (18)
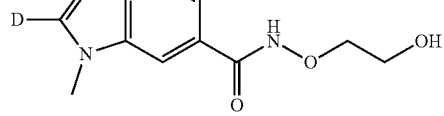
Formula (19)
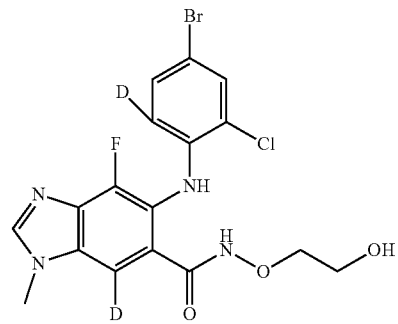
Formula (20)
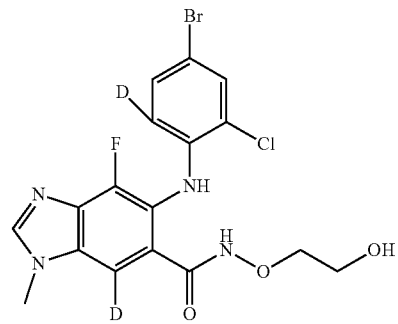
Formula (21)
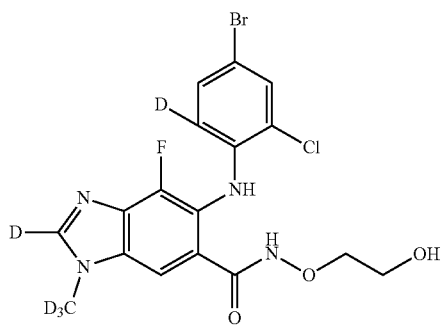
Formula (22)
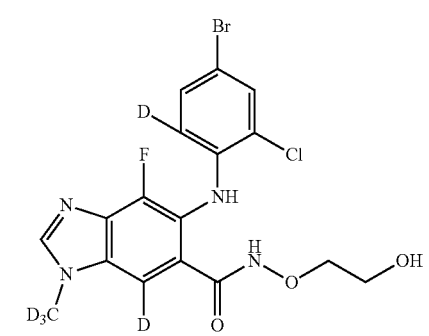
Formula (23)
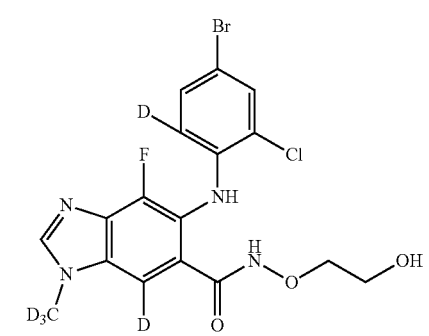
Formula (24)
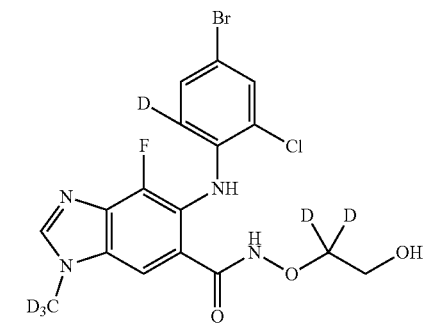
Formula (25)
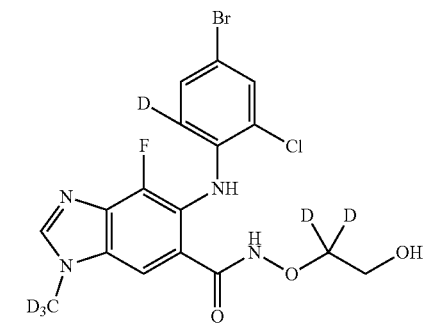

Formula (26)
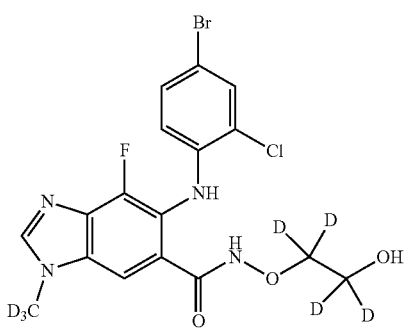

Formula (27)
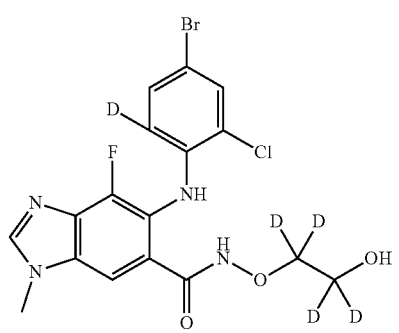

Formula (28)
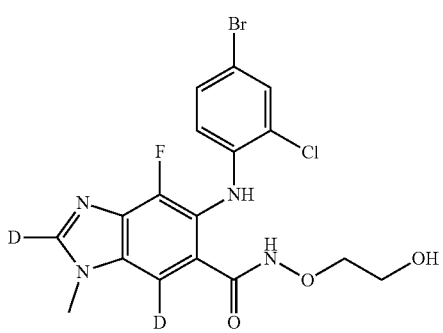

Formula (29)
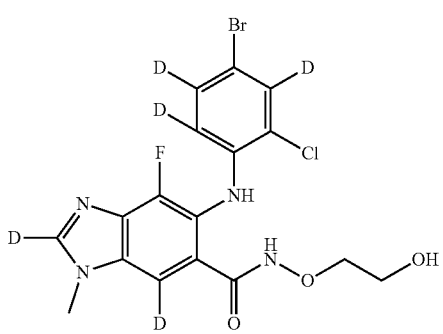

Formula (30)
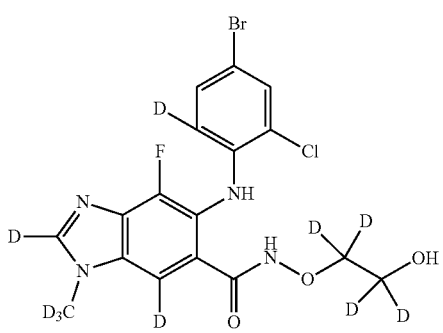

Formula (31)
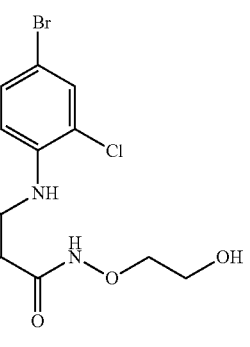

Formula (32)
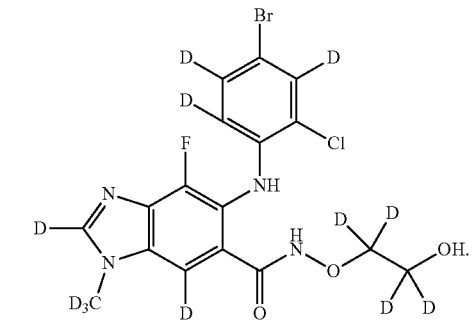

In another specific embodiment, the compounds do not include the non-deuterated compounds.

Pharmaceutical Compositions and Methods of Administration

In another aspect, provided herein is a pharmaceutical composition comprising the compound disclosed herein (also referred to as "active component") and pharmaceutically acceptable excipient(s). In some embodiments, the pharmaceutical composition comprises an effective amount of the active component. In some embodiments, the pharmaceutical composition comprises a therapeutically effective amount of the active component. In some embodiments, the pharmaceutical composition comprises a prophylactically effective amount of the active component.

The pharmaceutical composition disclosed herein comprises a safe and effective amount of the compound disclosed herein, or a pharmacologically acceptable salt thereof, and pharmacologically acceptable excipient(s) or carrier(s). By "safe and effective amount" it is meant that the amount of the compound is sufficient to significantly improve the condition without causing serious side effects. In general, the pharmaceutical composition contains from 0.5 to 2000 mg of the compound disclosed herein per dose, more preferably from 1 to 500 mg of the compound disclosed herein per dose. Preferably, the "one dose" is one capsule or tablet.

The "pharmaceutically acceptable excipient" refers to a non-toxic carrier, adjuvant or vehicle that does not destroy the pharmacological activity of the compound formulated together. Pharmaceutically acceptable carriers, adjuvants, or vehicles that can be used in the compositions disclosed herein include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based substances, polyethylene glycol, sodium carboxymethyl cellulose, polyacrylate, wax, polyethylene-polyoxypropylene block polymer, polyethylene glycol and lanolin.

The methods of administration of the compounds or pharmaceutical compositions disclosed herein are not particularly limited, and representative methods of administration include (but are not limited to): oral, duodenal, rectal, parenteral (intravenous, intramuscular or subcutaneous) and topical administration.

Solid dosage forms for oral administration include capsules, tablets, pills and granules. In these solid dosage forms, the active compound is mixed with at least one conventional inert excipient (or carrier), such as sodium citrate or dicalcium phosphate, or with the following ingredients: (a) fillers or solubilizers, such as starch, lactose, sucrose, glucose, mannitol and silicic acid; (b) binders, such as hydroxymethyl cellulose, alginate, gelatin, polyvinyl pyrrolidone, sucrose and gum arabic; (c) humectants, such as glycerol; (d) disintegrants, such as agar, calcium carbonate, potato starch, tapioca starch, alginic acid, certain complex silicates, and sodium carbonate; (e) retarding agents, such as paraffin wax; (f) absorption accelerators, such as quaternary amine compounds; (g) wetting agents, such as cetyl alcohol and glycerol monostearate; (h) adsorbents, such as kaolin; and (i) lubricants, such as talc, calcium stearate, magnesium stearate, solid polyethylene glycol, sodium dodecyl sulfate, or mixtures thereof. In capsules, tablets and pills, the dosage form may also contain buffers.

The solid dosage forms such as tablets, sugar pills, capsules, pills and granules may be prepared using coatings and shell materials, such as enteric coatings and other materials known in the art. They may contain opaque agents, and the active compound or compound in the composition may be released in a certain part of the digestive tract in a delayed manner. Examples of the embedding components that can be used are polymeric substances and waxy substances. If necessary, the active compound may also be formed into a microcapsule form with one or more of the excipients described above.

Liquid dosage forms for oral administration include pharmaceutically acceptable emulsions, solutions, suspensions, syrups or tinctures. In addition to the active compound, the liquid dosage forms may contain inert releasing agents conventionally used in the art, such as water or other solvents, solubilizers and emulsifiers, for example, ethanol, isopropanol, ethyl carbonate, ethyl acetate, propylene glycol, 1,3-butanediol, dimethylformamide and oil, especially cottonseed oil, peanut oil, corn germ oil, olive oil, castor oil, sesame oil, or mixtures of these substances.

In addition to these inert diluents, the composition may also contain adjuvants such as wetting agents, emulsifiers, suspending agents, sweeteners, flavoring agents and spices.

In addition to the active compound, the suspensions may contain suspending agents, such as ethoxylated isostearyl alcohol, polyoxyethylene sorbitol, sorbitan, microcrystalline cellulose, aluminum methoxide, agar, or mixtures of these substances, and the like.

The composition for parenteral injection may contain physiologically acceptable sterile aqueous or anhydrous solution(s), dispersion(s), suspension(s) or emulsion(s), and a sterile powder used for the redissolution into the sterile injectable solution(s) or dispersion(s). Suitable aqueous and anhydrous carriers, diluents, solvents or excipients include water, ethanol, polyol and suitable mixtures thereof.

The dosage forms of the compound disclosed herein for topical administration include ointments, powders, patches, sprays and inhalants. The active ingredient is mixed under the sterile conditions with physiologically acceptable carrier(s) and any preservative(s), buffer(s), or propellant(s) that may be required if necessary.

The compounds and compositions of the present disclosure may be administered alone, or may be advantageously administered in combination with other therapeutic agents currently available on the market or under development for the treatment of metabolic and/or liver disorders, such as metformin, insulin, thiazolidinediones, glitazones, statins, cholesterol inhibitors and/or other lipid-lowering drugs.

When using the pharmaceutical composition, a safe and effective amount of the compound disclosed herein is administrated to a mammal (such as a human) in need of treatment, wherein the dosage that administered is a pharmaceutically effective dosage. For a person of 60 kg body weight, the daily dose to be administered is usually 0.5 to 2000 mg, preferably 1 to 500 mg. Of course, the specific dosage should also take into account the factors such as the route of administration, patient's health status, etc., which are all within the scope of skills of the skilled physicians.

Treatment and Combination Therapy

The present disclosure also relates to a method of treating the hyperproliferative disease in a subject, which comprises administering to the subject a therapeutically effective amount of the compound disclosed herein, or the pharmaceutically acceptable salt, prodrug, hydrate, solvate, polymorph, stereoisomer or isotopic variant thereof, or the pharmaceutical composition disclosed herein. In one embodiment, the method relates to the treatment of cancers such as brain cancer, lung cancer, squamous cell carcinoma, bladder cancer, gastric cancer, pancreatic cancer, breast cancer, head cancer, neck cancer, kidney cancer, ovarian cancer, prostate cancer, colorectal cancer, esophageal cancer, testicular cancer, gynecology cancer or thyroid cancer. In another embodiment, the method is used in the treatment of non-cancerous hyperproliferative diseases such as benign hyperplasia of skin (such as psoriasis), restenosis, or prostate (e.g., benign prostatic hyperplasia (BPH)).

The present disclosure also relates to a method of treating the hyperproliferative disease in a subject, which comprises administering to the subject a therapeutically effective amount of the compound disclosed herein, or the pharmaceutically acceptable salt, prodrug, hydrate, solvate, polymorph, stereoisomer or isotopic variant thereof, or the pharmaceutical composition disclosed herein, or administering the compound disclosed herein, or the pharmaceutically acceptable salt, prodrug, hydrate, solvate, polymorph, stereoisomer or isotopic variant thereof and the anti-tumor agents selected from the group consisting of mitotic inhibitors, alkylating agents, antimetabolites, intercalating antibiotics, growth factor inhibitors, cell cycle inhibitors, enzyme inhibitors, topoisomerase inhibitors, biological response modifiers, anti-hormone drugs, angiogenesis inhibitors, and antiandrogens.

The present disclosure also relates to a method of treating the pancreatitis and kidney disease in a subject, which comprises administering to the subject a therapeutically effective amount of the compound disclosed herein, or the pharmaceutically acceptable salt, prodrug, hydrate, solvate, polymorph, stereoisomer or isotopic variant thereof, or the pharmaceutical composition disclosed herein.

The present disclosure also relates to a method of preventing the embryonic cell transplantation in a subject, which comprises administering to the subject a therapeutically effective amount of the compound disclosed herein, or the pharmaceutically acceptable salt, prodrug, hydrate, solvate, polymorph, stereoisomer or isotopic variant thereof, or the pharmaceutical composition disclosed herein.

The present disclosure also relates to a method of treating the disease related to vasculogenesis or angiogenesis in a subject, which comprises administering to the subject a therapeutically effective amount of the compound disclosed herein, or the pharmaceutically acceptable salt, prodrug, hydrate, solvate, polymorph, stereoisomer or isotopic variant thereof, or the pharmaceutical composition disclosed herein. In one embodiment, the method is used in the treatment of diseases selected from the group consisting of tumor angiogenesis, chronic inflammatory diseases such as rheumatoid arthritis, arteriosclerosis, inflammatory bowel disease, skin diseases such as psoriasis, rash and scleroderma, diabetes, diabetic retinitis, precocious retinitis, age-related muscle loss, hemangioma, glioma, melanoma, Kaposi's sarcoma, ovarian cancer, breast cancer, lung cancer, pancreas cancer, prostate cancer, colon cancer and epidermoid carcinoma.

According to the method of the present disclosure, the compound of the present disclosure, or the pharmaceutically acceptable salt, prodrug, hydrate, solvate, polymorph, stereoisomer or isotopic variant thereof, or the pharmaceutical composition disclosed herein, can be used in the treatment of the patients, for example, those who have been diagnosed with the following diseases: psoriasis, restenosis, atherosclerosis, BPH, lung cancer, hone cancer, CMML, pancreatic cancer, skin cancer, head and neck cancer, skin or intraocular melanoma, uterine cancer, ovarian cancer, rectal cancer, cancer in the anal area, gastric cancer, colon cancer, breast cancer, testicular cancer, gynecological tumors (such as uterine fibroids, fallopian tube cancer, endometrial cancer, cervical cancer, vaginal cancer or vulvar cancer), Hodgkin's disease, esophageal cancer, small intestine cancer, cancer of the endocrine system (such as thyroid cancer, parathyroid cancer or adrenal cancer), soft tissue sarcoma, lymphocytic lymphoma, bladder cancer, kidney or ureteral cancer (e.g., renal cell carcinoma, renal pelvis cancer), or cancer of the central nervous system (e.g., primary CNS lymphoma, spinal axis tumor, brainstem glioma, or pituitary carcinoma).

The present disclosure also relates to a pharmaceutical composition for inhibiting abnormal cell growth in a mammal, which comprises administering to the subject a therapeutically effective amount of the compound disclosed herein, or the pharmaceutically acceptable salt, prodrug, hydrate, solvate, polymorph, stereoisomer or isotopic variant thereof, and chemotherapeutic agent(s), wherein the amount of the compound disclosed herein, the salt, solvate or prodrug thereof and the amount of the chemotherapeutic agent(s) together can effectively inhibit the abnormal cell growth. Many chemotherapeutic agents are currently known in the art. In one embodiment, the chemotherapeutic agent is selected from the group consisting of mitotic inhibitors, alkylating agents, antimetabolites, intercalating antibiotics, growth factor inhibitors, cell cycle inhibitors, enzyme inhibitors, topoisomerase inhibitors, biological response modifiers, anti-hormone drugs, angiogenesis inhibitors, and antiandrogens.

The present disclosure also relates to a method of inhibiting the abnormal cell growth or treating the hyperproliferative disease in a subject, which comprises administering to the subject a therapeutically effective amount of the compound disclosed herein, or the pharmaceutically acceptable salt, prodrug, hydrate, solvate, polymorph, stereoisomer or isotopic variant thereof, in combination with the radiation therapy, wherein the amount of the compound disclosed herein, the salt, solvate or prodrug thereof and the radiation therapy together can effectively inhibit the abnormal cell growth or treat the hyperproliferative disease in the subject. Techniques for administering radiotherapeutic agents are known in the art, which can be used in the above combination therapy. The dosage of the compound disclosed herein in this combination therapy may be determined as follows.

It is believed that the compound of the present disclosure may make the abnormal cells more sensitive to the radiation therapy that is used to kill and/or inhibit the growth of such cells. Therefore, the present disclosure also relates to a method of making the abnormal cells in a mammal more sensitive to the radiation therapy, which includes administering to the subject a certain amount of the compound disclosed herein, or the pharmaceutically acceptable salt, prodrug, hydrate, solvate, polymorph, stereoisomer or isotopic variant thereof, or the pharmaceutical composition disclosed herein, wherein the amount is effective for increasing the sensitivity of the abnormal cells to the radiation therapy. In this method, the amount of the compound disclosed herein, the salt or solvate thereof may be determined according to the method of determining the effective amount of these compounds as described below.

Compared with the non-deuterated compounds known in the prior art, the compounds of the present disclosure have a series of advantages. The advantages of the present disclosure include: first, the compounds and compositions of the technical solutions disclosed herein provide a more advantageous therapeutic tool for the treatment of diseases caused by MEK. Second, the metabolism of the compound in the organism is improved, allowing the compound to have better pharmacokinetic characteristics. In this case, the dose may be changed and a long-acting formulation may be formed to improve the applicability. Third, the drug concentration of the compound in animals is increased, so that the efficacy of the drug is improved. Fourth, the safety of the compound may be increased due to the inhibition of certain metabolites.

EXAMPLES

The present disclosure is further illustrated below in conjunction with specific examples. It is to be understood that the examples are used to illustrate the present disclosure, and not intended to limit the scope of present disclosure. In the following examples, the experimental methods wherein the particular conditions are not specified are usually in accordance with conventional conditions or according to the conditions recommended by the manufacturer. Parts and percentages are parts by weight and percentage by weight unless otherwise stated.

Usually, in the preparation process, each reaction is usually carried out in an inert solvent at room temperature to reflux temperature (e.g., 0° C. to 100° C., preferably 0° C. to 80° C.). The reaction time is usually from 0.1 to 60 hours, preferably from 0.5 to 24 hours.

Example 1
Preparation of 6-(4-bromo-2-chloro-phenylamino)-7-fluoro-3-(methyl-d₃)-3H-benzimidazole-5-carboxylic acid (2-hydroxyethoxy)-amide (compound A-1)
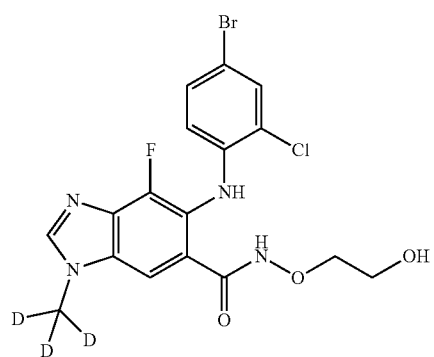
The following route was used for the synthesis:
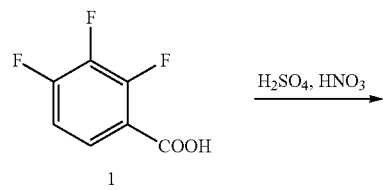
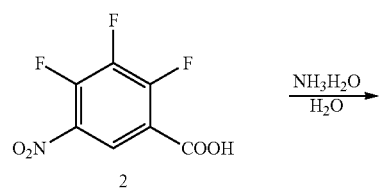
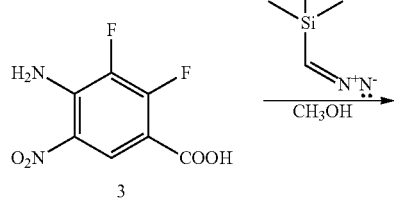
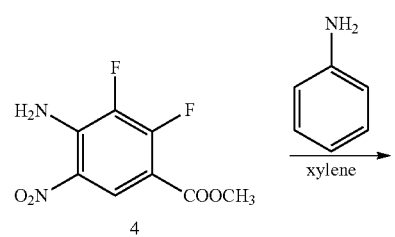
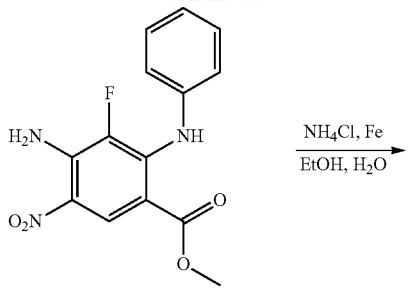
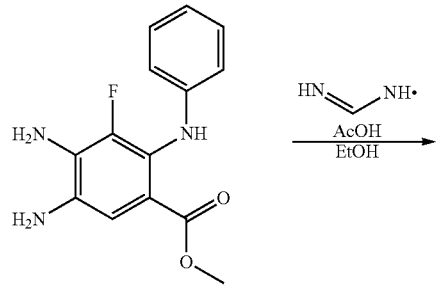
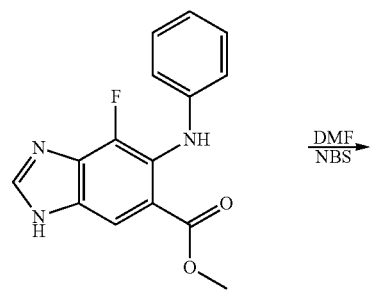
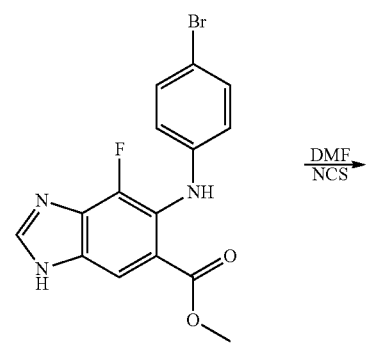
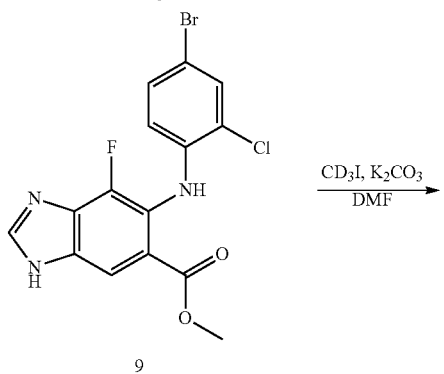

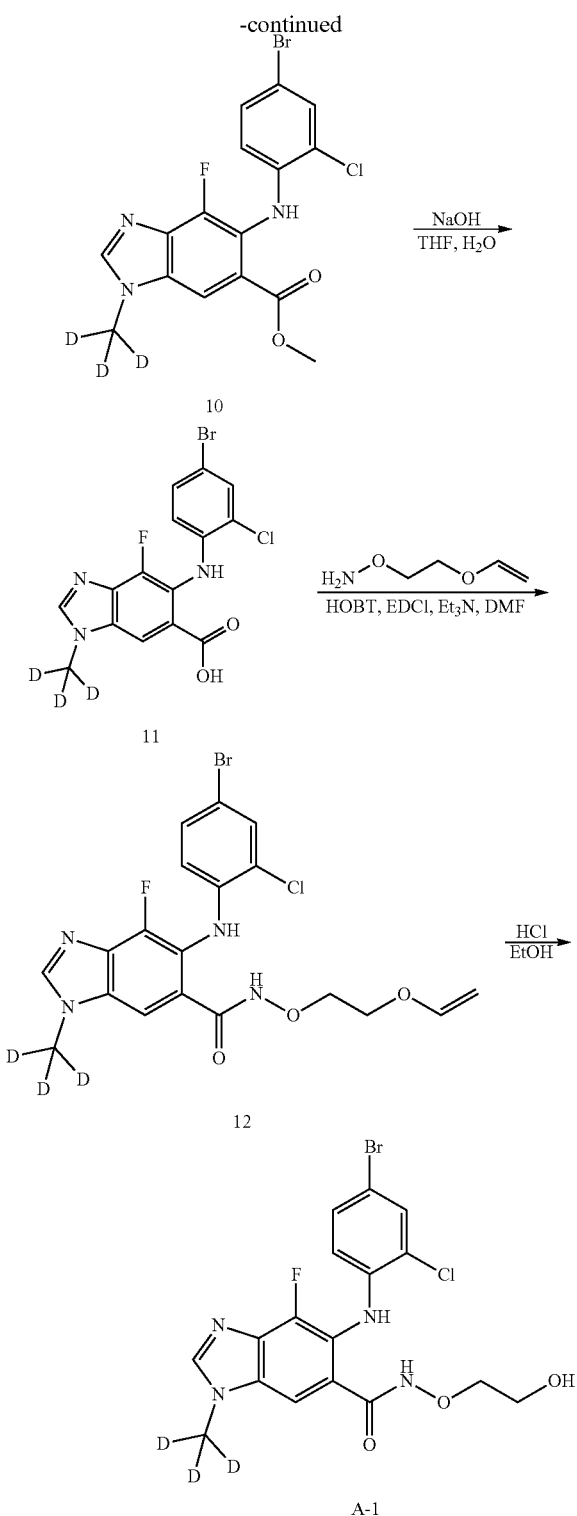

Step 1 Synthesis of Compound 2

Compound 1 (5 g, 28.41 mmol) was added to concentrated sulfuric acid (15 ml) solution, and heated to 90° C. Then a mixed acid of concentrated $H_2SO_4$ (3.2 g, 98%) and $HNO_3$ (3 g, 68%) was added dropwise, and the resulting mixture was reacted for 5 h. After cooling to room temperature, the resulting mixture was poured into ice water (80 ml) to quench the reaction. Ethyl acetate (80 ml×3) was added for extraction. The organic phases were combined, and dried over anhydrous sodium sulfate. The solvent was removed to give 5.5 g of oil, with a yield of 88%. LC-MS (APCI): m/z=222.06 (M+1)$^+$.

Step 2 Synthesis of Compound 3

At 0° C., $NH_3 \cdot H_2O$ (2.38 g, 67.87 mmol) was slowly added dropwise to a solution of compound 2 (3 g, 13.57 mmol) in water, after which, the reaction was continued for 6 h. 1 M hydrochloric acid was added to quench the reaction until the pH of the solution reached about 2. Dichloromethane (60 ml×3) was added for extraction. The organic phases were combined, and dried over anhydrous sodium sulfate. The solvent was removed to give 2.4 g of a light yellow solid product, with a yield of 81%.

Step 3 Synthesis of Compound 4

At 0° C., trimethylsilyldiazomethane (1.26 g, 11.02 mmol) was slowly added dropwise to a solution of compound 3 (2.0 g, 9.17 mmol) in methanol, after which, the reaction was continued for 1 h. A few drops of acetic acid were added to quench the reaction, and most of the methanol was dried with a rotary evaporator. Then water (20 ml) was added, and the resulting mixture was extracted with dichloromethane (40 ml×3). The organic phases were combined, and dried over anhydrous sodium sulfate. The solvent was removed to give a light yellow solid, and then methanol (10 ml) was added to form a slurry, and to give 1.8 g of a pure product, with a yield of 84%.

Step 4 Synthesis of Compound 5

Compound 4 (1.0 g, 4.31 mmol) and aniline (2.0 g, 21.55 mmol) were sequentially added to xylene. After stirring at 125° C. for 10 h, the reaction solution was cooled to room temperature. Most of the solvent was removed, and the residue was extracted with dichloromethane (30 ml×3). The organic phases were combined, and dried over anhydrous sodium sulfate. The solvent was removed to give a light yellow solid, and then petroleum ether (20 ml) was added to form a slurry, and to give 1.1 g of a pure substance, with a yield of 83%. LC-MS (APCI): m/z=306.13 (M+1)$^+$.

Step 5 Synthesis of Compound 6

Ammonium chloride (1.05 g, 19.67 mmol) and iron powder (1.10 g, 19.67 mmol) were sequentially added to a solution of compound 5 (1.0 g, 3.28 mmol) in mixture of ethanol (15 ml) and water (5 ml). After stirring at 70° C. for 0.5 h, the reaction solution was cooled to room temperature. Most of the solvent was removed, and the residue was extracted with dichloromethane (30 ml×3). The organic phases were combined, and dried over anhydrous sodium sulfate. The solvent was removed to give 0.65 g of an off-white solid, with a yield of 72%. LC-MS (APCI): m/z=276.27 (M+1)$^+$.

Step 6 Synthesis of Compound 7

Compound 6 (0.8 g, 2.91 mmol) and formamidine acetate (0.36 g, 3.49 mmol) were sequentially added to ethanol (20 ml). After stirring at 80° C. for 8 h, the reaction solution was cooled to room temperature. Most of the solvent was removed, and the residue was extracted with dichloromethane (20 ml×3). The organic phases were combined, and dried over anhydrous sodium sulfate. The solvent was removed to give 0.63 g of an off-white solid product, with a yield of 76%. LC-MS (APCI): m/z=286.39 (M+1)$^+$.

Step 7 Synthesis of Compound 8

N-bromosuccinimide (0.69 g, 3.85 mmol) was added to a solution of compound 7 (1.1 g, 3.85 mmol) in DMF (15 ml), and the reaction solution was stirred and reacted at room temperature for 4 h. Water (30 ml) was added to quench the reaction, and dichloromethane (30 ml×3) was added for extraction. The organic phases were combined, washed twice with saturated sodium chloride, and dried over anhydrous sodium sulfate. The solvent was removed to give 1.2 g of a gray solid, with a yield of 86%. LC-MS (APCI): m/z=365.08 (M+1)$^+$.

Step 8 Synthesis of Compound 9

N-chlorosuccinimide (0.44 g, 3.30 mmol) was added to a solution of compound 8 (1.2 g, 3.30 mmol) in DMF (15 ml), and the reaction solution was stirred and reacted at room temperature for 10 h. Water (30 ml) was added to quench the reaction, and dichloromethane (30 ml×3) was added for extraction. The organic phases were combined, washed twice with saturated sodium chloride, and dried over anhydrous sodium sulfate. The solvent was removed to give 1.0 g of a gray solid, with a yield of 76%. LC-MS (APCI): m/z=398.35 (M+1)$^+$. $^1$H NMR (400 MHz, DMSO) δ 13.06 (s, 1H), 8.48 (s, 1H), 8.07 (d, J=35.9 Hz, 2H), 7.63 (d, J=2.0 Hz, 1H), 7.28 (dd, J=2.2 Hz, 1H), 6.46 (s, 1H), 3.82 (s, 3H).

Step 9 Synthesis of Compound 10

Compound 9 (1.0 g, 2.51 mmol), deuterated iodomethane (0.44 g, 3.01 mmol) and potassium carbonate (0.70 g, 5.03 mmol) were sequentially added to DMF (15 ml), and the reaction solution was reacted at 70° C. for 3 h. After cooling to room temperature, water (30 ml) was added to quench the reaction, and the resulting mixture was extracted with ethyl acetate (40 ml×3). The organic phases were combined, and dried over anhydrous sodium sulfate. The solvent was removed, and the concentrate was separated by column (eluent: petroleum ether/ethyl acetate (v/v)=4:1) to give 0.4 g of an off-white solid, with a yield of 38%. LC-MS (APCI): m/z=416.51 (M+1)$^+$.

Step 10 Synthesis of Compound 11

Sodium hydroxide (0.15 g, 3.85 mmol) and water (5 ml) were sequentially added to a solution of compound 10 (0.40 g, 0.96 mmol) in tetrahydrofuran (15 ml), and the reaction solution was stirred at 45° C. for 10 h. After cooling to room temperature, most of the solvent was removed, and the pH value of the residue was adjusted to 2 with 2 M hydrochloric acid. Dichloromethane (30 ml×3) was added for extraction. The organic phases were combined, and dried over anhydrous sodium sulfate. The solvent was removed to give 0.30 g of a white solid, with a yield of 79%.

Step 11 Synthesis of Compound 12

Compound 11 (0.20 g, 0.50 mmol), 1-[2-(aminooxy)ethoxy]ethylene (0.062 g, 0.60 mmol), 1-(3-dimethylaminopropyl)-3-ethylcarbodiimide hydrochloride (EDCI, 0.114 g, 0.60 mmol), triethylamine (0.104 g, 1.0 mmol) and 1-hydroxybenzotriazole (HOBT, 0.068 g, 0.60 mmol) were sequentially added to DMF (10 ml), and the resulting mixture was stirred at room temperature for 10 h. Water (30 ml) was added to quench the reaction, and ethyl acetate (15 ml×3) was added for extraction. The organic phases were combined, and dried over anhydrous sodium sulfate. The solvent was removed, and the concentrate was separated by column (eluent: ethyl acetate/methanol (v/v)=40:1) to give 0.15 g of a white solid, with a yield of 62%. LC-MS (APCI): m/z=488.59 (M+1)$^+$.

Step 12 Synthesis of compound A-1

At 0° C., 1 M hydrochloric acid (3 ml) solution was slowly added to a solution of compound 12 (0.15 g, 0.30 mmol) in ethanol (10 ml), and the resulting mixture was warmed to room temperature and reacted for 8 h. Most of the solvent was dried with a rotary evaporator, and the resulting solution was extracted three times with 20 ml of ethyl acetate and tetrahydrofuran ((v/v)=3:1). The organic phases were combined, dried over anhydrous sodium sulfate, and the concentrate was separated by column (eluent: ethyl acetate/methanol (v/v)=20:1) to give 60 mg of a white solid, with a yield of 41%. LC-MS (APCI): m/z=461.52 (M+1)$^+$.

$^1$H NMR (400 MHz, DMSO) δ 12.23 (s, 1H), 8.26 (s, 1H), 8.17 (s, 1H), 7.63 (s, 1H), 7.58 (d, 1H), 7.24 (dd, 1H), 6.50 (dd, 1H), 3.73 (m, 2H), 3.35 (m, 2H).

Example 2

Preparation of 6-(4-bromo-2-chloro-6-d-phenylamino)-7-fluoro-3-methyl-3H-benzimidazole-5-carboxylic acid (2-hydroxyethoxy)amide (compound A-2)

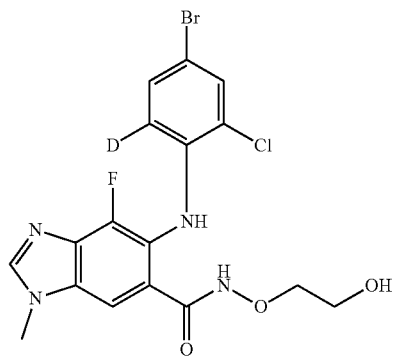

The following route was used for the synthesis:

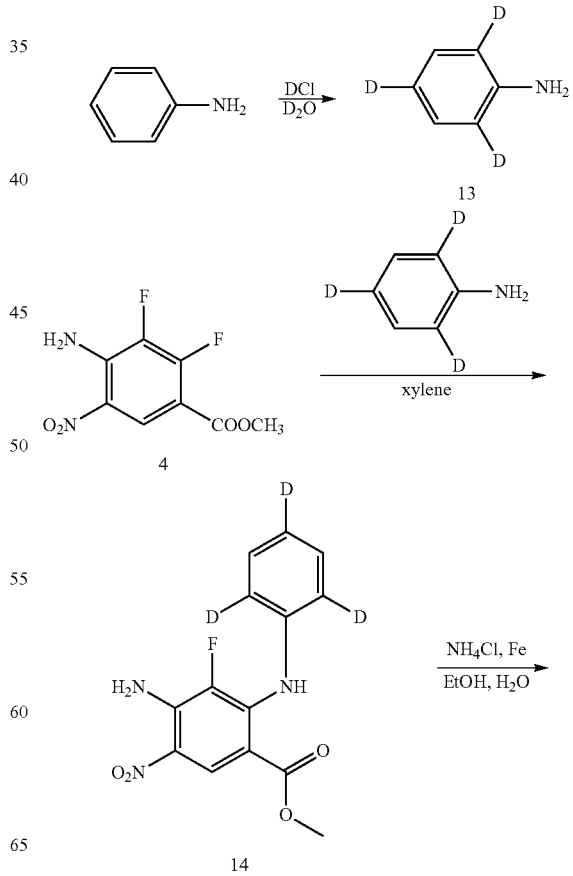

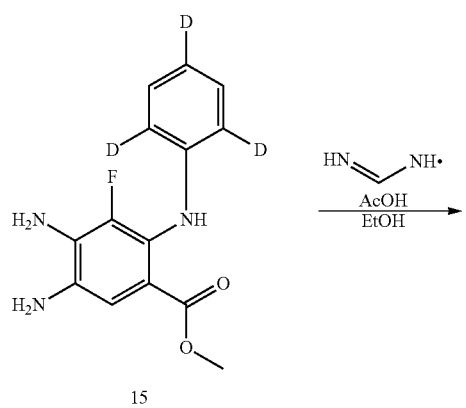
15
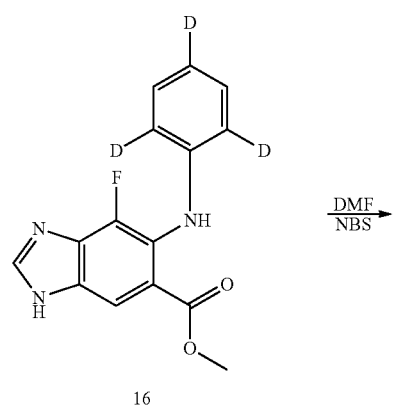
16
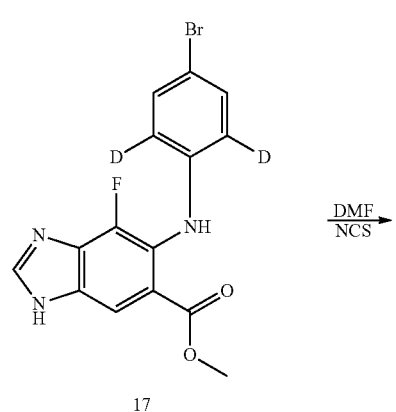
17
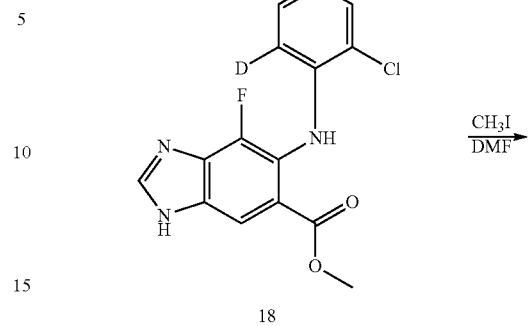
18
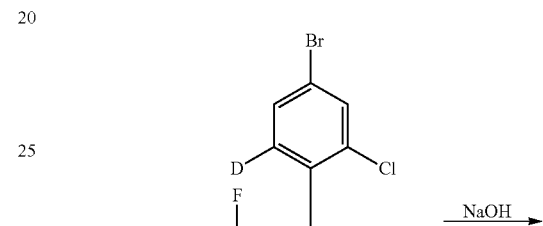
19
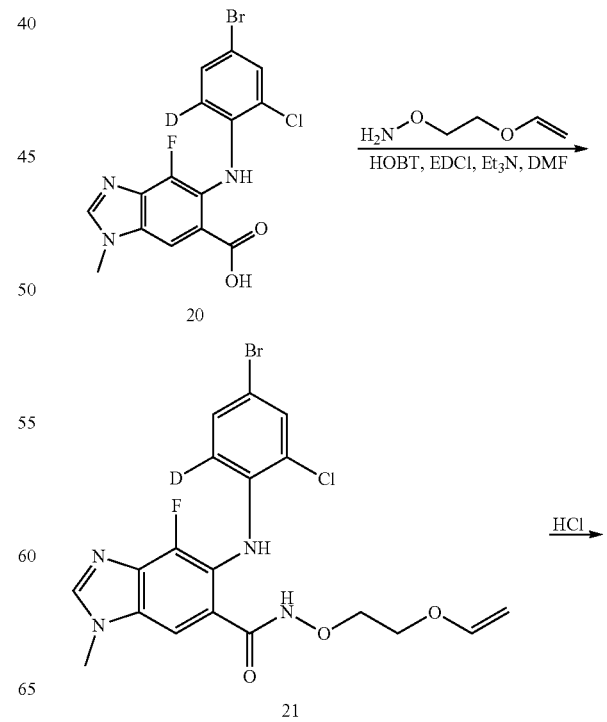
20
21

-continued

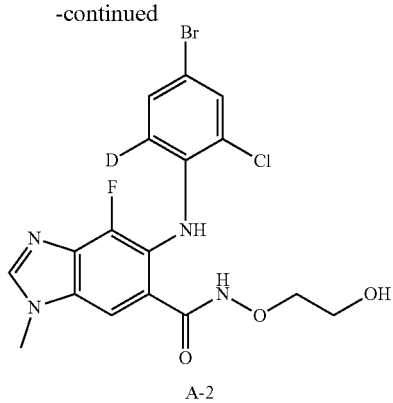

A-2

Step 1 Synthesis of Compound 13

Aniline (2.0 g, 21.51 mmol) and deuterium chloride (0.86 g, 23.66 mmol) were sequentially added to the heavy water (10 ml). The reaction solution was reacted in microwave at 160° C. for 1 h, and cooled to room temperature. The reaction solution was adjusted to neutral with 2 M sodium hydroxide, and extracted with dichloromethane (30 ml×3). The organic phases were combined, and dried over anhydrous sodium sulfate. The solvent was removed to give 1.8 g of brown oil, with a yield of 89%.

Step 2 Synthesis of Compound 14

Compound 4 (0.8 g, 3.45 mmol) and compound 13 (1.66 g, 17.24 mmol) were sequentially added to xylene (20 ml). After stirring at 125° C. for 10 h, the reaction solution was cooled to room temperature. Most of the solvent was removed, and the residue was extracted with dichloromethane (30 ml×3). The organic phases were combined, and dried over anhydrous sodium sulfate. The solvent was removed to give a light yellow solid, and the petroleum ether (20 ml) was added to form a slurry, and gave 0.8 g of a pure substance, with a yield of 75%. LC-MS (APCI): m/z=309.10 $(M+1)^+$.

Step 3 Synthesis of Compound 15

Ammonium chloride (0.84 g, 15.58 mmol) and iron powder (0.87 g, 15.58 mmol) were sequentially added to a solution of compound 14 (0.8 g, 2.60 mmol) in mixture of ethanol (15 ml) and water (5 ml). After stirring at 70° C. for 0.5 h, the reaction solution was cooled to room temperature. Most of the solvent was removed, and the residue was extracted with dichloromethane (30 ml×3). The organic phases were combined, and dried over anhydrous sodium sulfate. The solvent was removed to give 0.60 g of an off-white solid, with a yield of 83%. LC-MS (APCI): m/z=279.13 $(M+1)^+$.

Step 4 Synthesis of Compound 16

Compound 15 (0.6 g, 2.16 mmol) and formamidine acetate (0.27 g, 2.59 mmol) were sequentially added to ethanol (15 ml). After stirring at 80° C. for 8 h, the reaction solution was cooled to room temperature. Most of the solvent was removed, and the residue was extracted with dichloromethane (20 ml×3). The organic phases were combined, and dried over anhydrous sodium sulfate. The solvent was removed to give 0.58 g of an off-white solid product, with a yield of 92%. LC-MS (APCI): m/z=290.06 $(M+1)^+$.

Step 5 Synthesis of Compound 17

N-bromosuccinimide (0.36 g, 2.01 mmol) was added to a solution of compound 16 (0.58 g, 2.01 mmol) in DMF (10 ml), and the reaction solution was stirred and reacted at room temperature for 4 h. Water (20 ml) was added to quench the reaction, and dichloromethane (20 ml×3) was added for extraction. The organic phases were combined, washed twice with saturated sodium chloride, and dried over anhydrous sodium sulfate. The solvent was removed to give 0.56 g of a gray solid, with a yield of 78%.

Step 6 Synthesis of Compound 18

N-chlorosuccinimide (NCS, 0.21 g, 1.53 mmol) was added to a solution of compound 17 (0.56 g, 1.53 mmol) in DMF (10 ml), and the reaction solution was stirred and reacted at room temperature for 10 h. Water (20 ml) was added to quench the reaction, and dichloromethane (20 ml×3) was added for extraction. The organic phases were combined, washed twice with saturated sodium chloride, and dried over anhydrous sodium sulfate. The solvent was removed to give 0.5 g of a gray solid, with a yield of 82%. LC-MS (APCI): m/z=400.05 $(M+1)^+$.

Step 7 Synthesis of Compound 19

Compound 18 (0.5 g, 1.25 mmol), iodomethane (0.22 g, 1.50 mmol) and potassium carbonate (0.35 g, 2.50 mmol) were sequentially added to DMF (10 ml), and the reaction solution was reacted at 70° C. for 3 h. After cooling to room temperature, water (10 ml) was added to quench the reaction, and the resulting mixture was extracted with ethyl acetate (20 ml×3). The organic phases were combined, and dried over anhydrous sodium sulfate. The solvent was removed, and the concentrate was separated by column (eluent: petroleum ether/ethyl acetate (v/v)=4:1) to give 0.18 g of an off-white solid, with a yield of 34%. LC-MS (APCI): m/z=414.11 $(M+1)^+$.

Step 8 Synthesis of Compound 20

Sodium hydroxide (0.087 g, 2.18 mmol) and water (3 ml) were sequentially added to a solution of compound 19 (0.18 g, 0.44 mmol) in tetrahydrofuran (9 ml), and the reaction solution was stirred at 45° C. for 10 h. After cooling to room temperature, most of the solvent was removed, and the pH value of the residue was adjusted to 2 with 2 M hydrochloric acid. Dichloromethane (10 ml×3) was added for extraction. The organic phases were combined, and dried over anhydrous sodium sulfate. The solvent was removed to give 0.12 g of a white solid, with a yield of 68%.

Step 9 Synthesis of Compound 21

Compound 20 (0.12 g, 0.30 mmol), 1-[2-(aminooxy)ethoxy]ethylene (0.038 g, 0.36 mmol), 1-(3-dimethylaminopropyl)-3-ethylcarbodiimide hydrochloride (EDCI, 0.07 g, 0.36 mmol), triethylamine (0.061 g, 0.60 mmol) and 1-hydroxybenzotriazole (HOBT, 0.049 g, 0.36 mmol) were sequentially added to DMF (10 ml), and the resulting mixture was stirred at room temperature for 10 h. Water (10 ml) was added to quench the reaction, and ethyl acetate (15 ml×3) was added for extraction. The organic phases were combined, and dried over anhydrous sodium sulfate. The solvent was removed, and the concentrate was separated by column (eluent: ethyl acetate/methanol (v/v)=40:1) to give 0.10 g of a white solid, with a yield of 68%. LC-MS (APCI): m/z=485.86 $(M+1)^+$.

Step 10 Synthesis of compound A-2

At 0° C., 1 M hydrochloric acid (2 ml) was slowly added to a solution of compound 21 (0.10 g, 0.20 mmol) in ethanol (10 ml), and the resulting mixture was warmed to room temperature and reacted for 8 h. Most of the solvent was dried with a rotary evaporator, and the resulting solution was extracted three times with 20 ml of ethyl acetate and tetrahydrofuran ((v/v)=3:1). The organic phases were combined, dried over anhydrous sodium sulfate, and the concentrate was separated by column (eluent: ethyl acetate/methanol (v/v)=20:1) to give 45 mg of a white solid, with a yield of 48%. LC-MS (APCI): m/z=459.61 (M+1)$^+$. $^1$H NMR (400 MHz, DMSO) δ 12.23 (s, 1H), 8.24 (s, 1H), 8.07 (s, 1H), 7.83 (s, 1H), 7.58 (s, 1H), 7.34 (s, 1H), 3.85 (s, 3H), 3.68 (m, 2H), 3.30 (m, 2H).

Example 3

Preparation of 6-(4-bromo-2-chloro-6-d-phenylamino)-7-fluoro-3-(methyl-d$_3$)-3H-benzimidazole-5-carboxylic acid (2-hydroxyethoxy)amide (compound A-3)

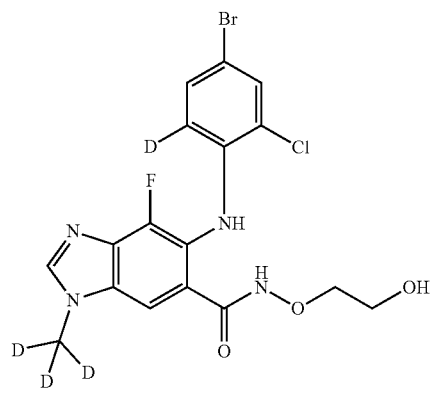

The following route was used for the synthesis:

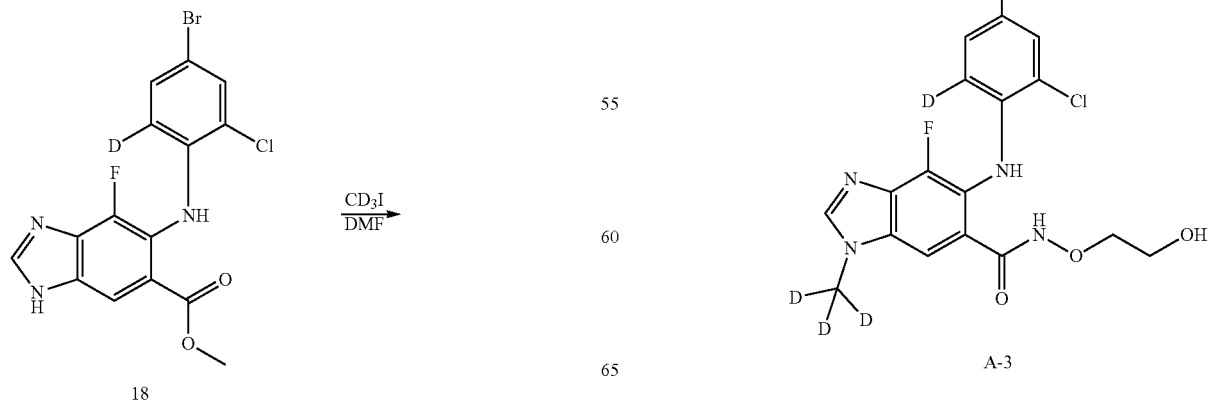

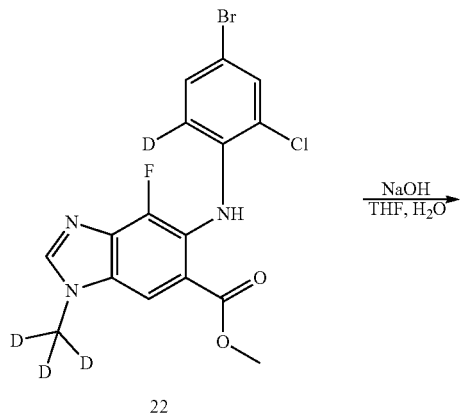

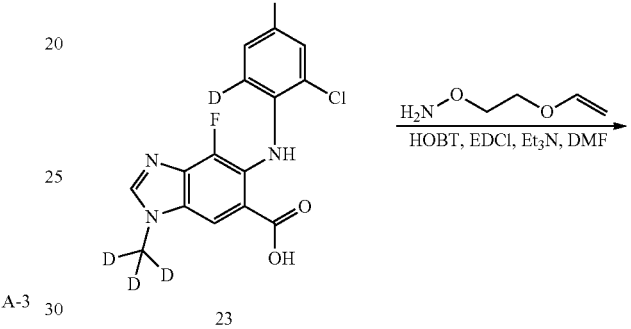

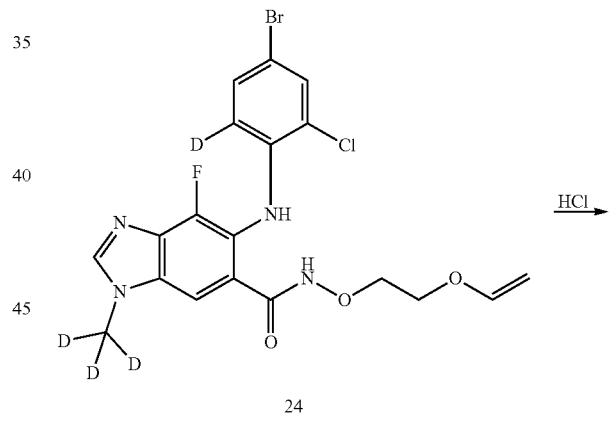

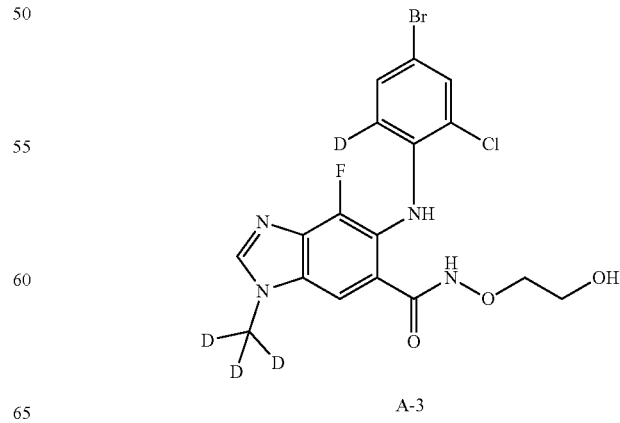

Step 1 Synthesis of Compound 22

Compound 18 (0.6 g, 1.51 mmol), deuterated iodomethane (0.26 g, 1.80 mmol) and potassium carbonate (0.42 g, 3.03 mmol) were sequentially added to DMF (15 ml), and the reaction solution was reacted at 70° C. for 3 h. After cooling to room temperature, water (20 ml) was added to quench the reaction, and the resulting mixture was extracted with ethyl acetate (30 ml×3). The organic phases were combined, and dried over anhydrous sodium sulfate. The solvent was removed, and the concentrate was separated by column (eluent: petroleum ether/ethyl acetate (v/v)=4:1) to give 0.25 g of an off-white solid, with a yield of 40%. LC-MS (APCI): tri/z=417.39 $(M+1)^+$.

Step 2 Synthesis of Compound 23

Sodium hydroxide (0.120 g, 3.00 mmol) and water (5 ml) were sequentially added to a solution of compound 22 (0.25 g, 0.60 mmol) in tetrahydrofuran (15 ml), and the reaction solution was stirred at 45° C. for 10 h. After cooling to room temperature, most of the solvent was removed, and the pH value of the residue was adjusted to 2 with 2 M hydrochloric acid. Dichloromethane (15 ml×3) was added for extraction. The organic phases were combined, and dried over anhydrous sodium sulfate. The solvent was removed to give 0.15 g of a white solid, with a yield of 62%.

Step 3 Synthesis of Compound 24

Compound 23 (0.15 g, 0.37 mmol), 1-[2-(aminooxy)ethoxy]ethylene (0.046 g, 0.45 mmol), 1-(3-dimethylaminopropyl)-3-ethylcarbodiimide hydrochloride (EDCI, 0.086 g, 0.45 mmol), triethylamine (0.075 g, 0.74 mmol) and 1-hydroxybenzotriazole (HOBT, 0.061 g, 0.45 mmol) were sequentially added to DMF (10 ml), and the resulting mixture was stirred at room temperature for 10 h. Water (10 ml) was added to quench the reaction, and ethyl acetate (15' ml×3) was added for extraction. The organic phases were combined, and dried over anhydrous sodium sulfate. The solvent was removed, and the concentrate was separated by column (eluent: ethyl acetate/methanol (v/v)=40:1) to give 0.13 g of a white solid, with a yield of 72%. LC-MS (APCI): m/z=488.49 $(M+1)^+$.

Step 4 Synthesis of Compound A-3

At 0° C., 1 M hydrochloric acid (2 ml) solution was slowly added to a solution of compound 24 (0.13 g, 0.27 mmol) in ethanol (10 ml), and the resulting mixture was warmed to room temperature and reacted for 8 h. Most of the solvent was dried with a rotary evaporator, and the resulting solution was extracted three times with 20 ml of ethyl acetate and tetrahydrofuran ((v/v)=3:1). The organic phases were combined, dried over anhydrous sodium sulfate, and the concentrate was separated by column (eluent: ethyl acetate/methanol (v/v)=20:1) to give 50 mg of a white solid, with a yield of 40%. LC-MS (APCI): m/z=462.57 $(M+1)^+$. $^1$H NMR (400 MHz, DMSO) δ 12.23 (s, 1H), 8.25 (s, 1H), 8.09 (s, 1H), 7.83 (s, 1H), 7.60 (s, 1H), 7.34 (s, 1H), 3.81 (m, 2H), 3.35 (m, 2H).

Example 4

Preparation of 6-(4-bromo-2-chlorophenylamino)-7-fluoro-3-methyl-3H-benzimidazole-5-carboxylic acid (2-hydroxyethoxy-2,2-$d_2$)amide (compound A-4)

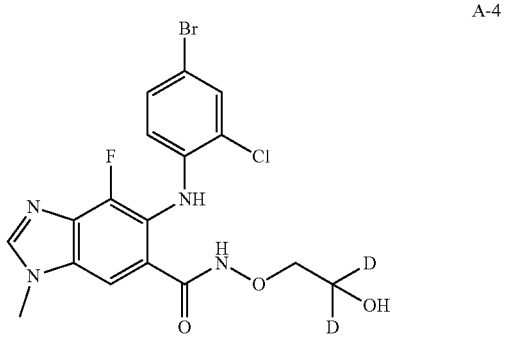 [SMILES: [2H]C([2H])(O)CONC(=O)c1cc2c(ncn2C)c(F)c1Nc1ccc(Br)cc1Cl]

A-4

The following route was used for the synthesis:

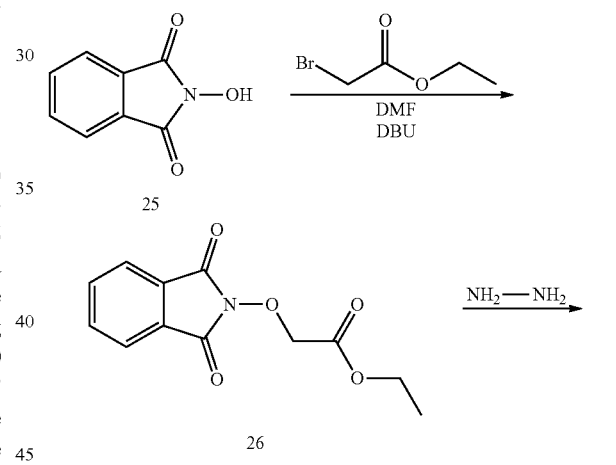

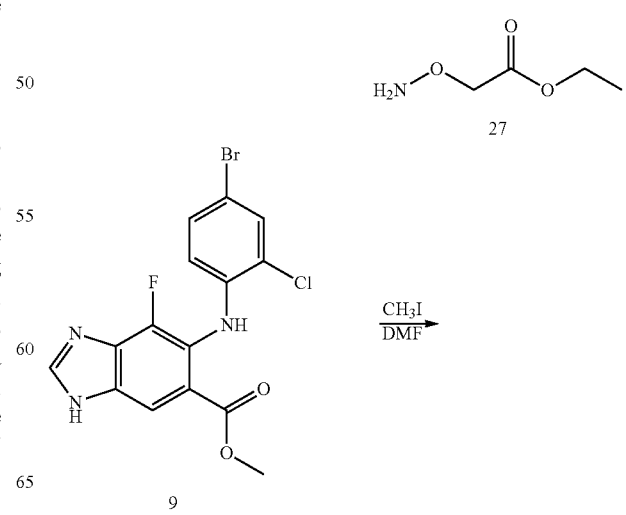

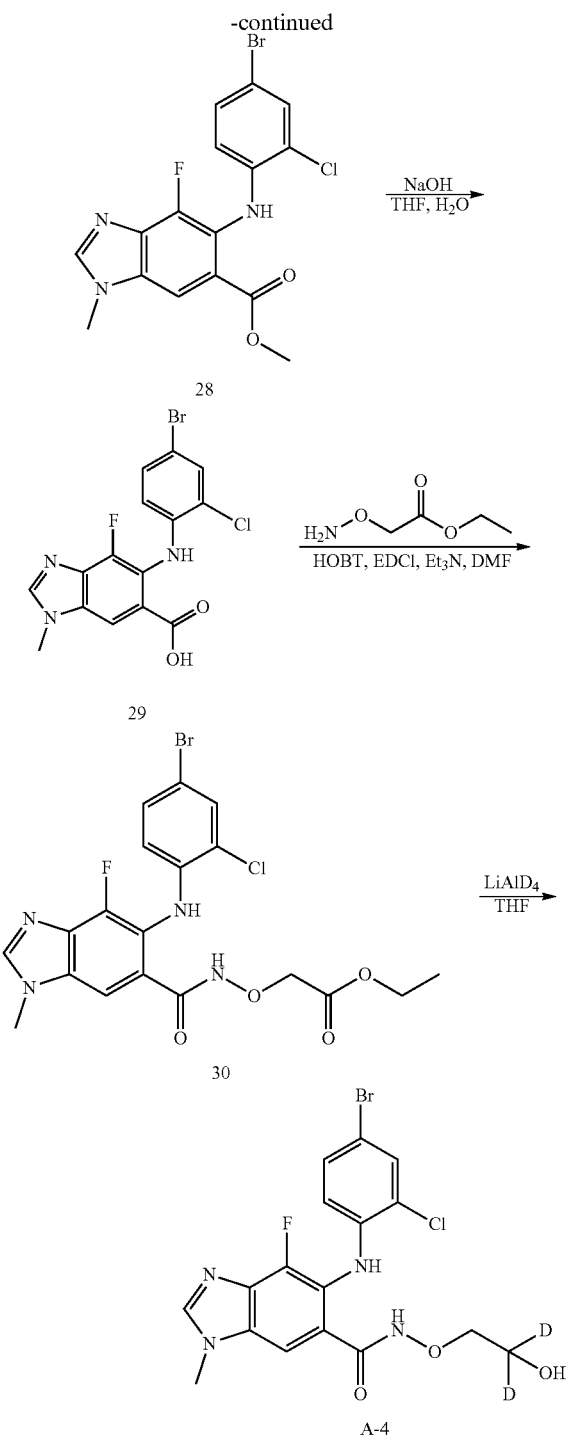

Step 1 Synthesis of Compound 26

At room temperature, ethyl bromoacetate (3.09 g, 20.2 mmol) was slowly added dropwise to a solution of compound 25 (3.0 g, 18.4 mmol) and 1,8-diazabicycloundec-7-ene (DBU, 4.20 g, 27.6 mmol) in DMF (50 mL), after which, the reaction solution was reacted overnight. Water (50 ml) was added to quench the reaction, and the resulting mixture was extracted with ethyl acetate (50 ml×3). The organic phases were combined, washed with water, and dried over anhydrous sodium sulfate. The solvent was removed to give a white solid, and then 50 ml of solvent containing petroleum ether and ethyl acetate ((v/v)=5:1) was added to form a slurry, which was filtered to give 3.2 g of a white solid product, with a yield of 71%.

Step 2 Synthesis of Compound 27

At room temperature, hydrazine hydrate (0.48 g, 9.64 mmol) was slowly added dropwise to a solution of compound 26 (2.0 g, 8.04 mmol) in dichloromethane (20 mL), after which, the reaction was continued for 4 h. After the filtration, the filtrate was dried with a rotary evaporator. Then n-hexane (20 ml) was added to the residue, stirring for 2 h to form a slurry. After the filtration, the filtrate was dried with a rotary evaporator to give 0.3 g of an oil product, with a yield of 32%. LC-MS (APCI): m/z=120.07 (M+1)$^+$.

Step 3 Synthesis of Compound 28

Compound 9 (0.7 g, 1.76 mmol), iodomethane (0.30 g, 2.11 mmol) and potassium carbonate (0.49 g, 3.52 mmol) were sequentially added to DMF (15 ml), and the reaction solution was reacted at 70° C. for 3 h. After cooling to room temperature, water (20 ml) was added to quench the reaction, and the resulting mixture was extracted with ethyl acetate (30 ml×3). The organic phases were combined, and dried over anhydrous sodium sulfate. The solvent was removed, and the concentrate was separated by column (eluent: petroleum ether/ethyl acetate (v/v)=4:1) to give 0.30 g of an off-white solid, with a yield of 42%. LC-MS (APCI): m/z=413.08 (M+1)$^+$.

Step 4 Synthesis of Compound 29

Sodium hydroxide (0.146 g, 3.64 mmol) and water (5 ml) were sequentially added to a solution of compound 28 (0.30 g, 0.73 mmol) in tetrahydrofuran (15 ml), and the reaction solution was stirred at 45° C. for 10 h. After cooling to room temperature, most of the solvent was removed, and the pH value of the residue was adjusted to 2 with 2 M hydrochloric acid. Dichloromethane (10 ml×3) was added for extraction. The organic phases were combined, and dried over anhydrous sodium sulfate. The solvent was removed to give 0.21 g of a white solid, with a yield of 72%. LC-MS (APCI): m/z=399.25 (M+1)$^+$.

Step 5 Synthesis of Compound 30

Compound 29 (0.20 g, 0.50 mmol), compound 27 (0.12 g, 1.0 mmol), 1-(3-dimethylaminopropyl)-3-ethylcarbodiimide hydrochloride (EDCI, 0.115 g, 0.60 mmol), triethylamine (0.102 g, 1.0 mmol) and 1-hydroxybenzotriazole (HOBT, 0.081 g, 0.60 mmol) were sequentially added to DMF (10 ml), and the resulting mixture was stirred at room temperature for 10 h. Water (10 ml) was added to quench the reaction, and ethyl acetate (15 ml×3) was added for extraction. The organic phases were combined, and dried over anhydrous sodium sulfate. The solvent was removed, and the concentrate was separated by column (eluent: ethyl acetate/methanol (v/v)=50:1) to give 0.15 g of a white solid, with a yield of 63%. LC-MS (APCI): m/z=486.51 (M+1)$^+$.

Step 6 Synthesis of compound A-4

At 0° C., LiAlD$_4$ (0.025 g, 0.62 mmol) was added to a solution of compound 30 (0.15 g, 0.31 mmol) in tetrahydrofuran (10 ml), after which, the reaction was continued for 0.5 h. 1 M hydrochloric acid (10 ml) was added to quench the reaction, and the resulting mixture was extracted with ethyl acetate (20 ml×3). The organic phases were combined, dried over anhydrous sodium sulfate, and the concentrate was separated by column (eluent: ethyl acetate/methanol (v/v)=20:1) to give 45 mg of a white solid, with a yield of 31%. LC-MS (APCI): m/z=460.21 (M+1)$^+$. $^1$H NMR (400 MHz, DMSO) δ 11.83 (s, 1H), 8.22 (s, 1H), 8.18 (s, 1H), 7.83 (s, 1H), 7.62 (d, 1H), 7.21 (dd, 1H), 6.69 (dd, 1H), 3.95 (s, 3H) 3.82 (s, 2H).

Example 5

Preparation of 6-(4-bromo-2-chlorophenylamino)-7-fluoro-3-(methyl-d₃)-3H-benzimidazole-5-carboxylic acid (2-hydroxyethoxy-2,2-d₂)amide (compound A-5)

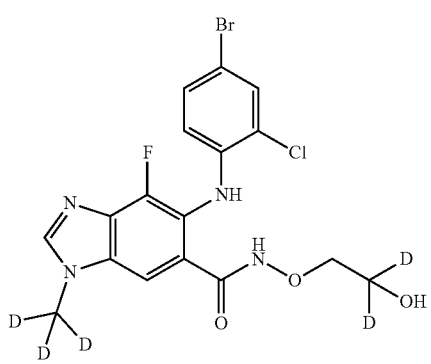

A-5

The following route was used for the synthesis:

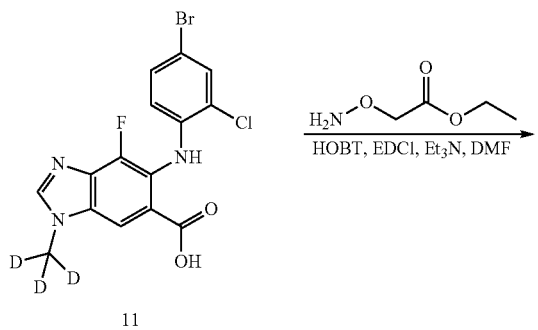

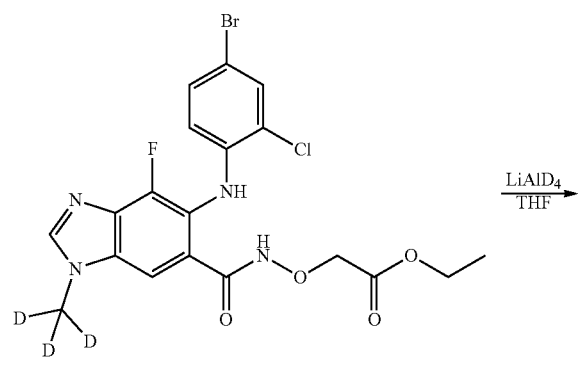

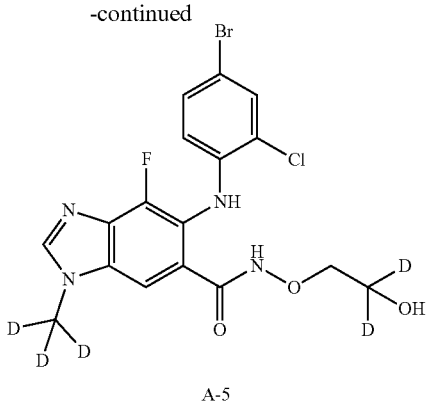

A-5

Step 1 Synthesis of Compound 31

Compound 11 (0.30 g, 0.75 mmol), compound 27 (0.179 g, 1.50 mmol), 1-(3-dimethylaminopropyl)-3-ethylcarbodiimide hydrochloride (EDCI, 0.173 g, 0.90 mmol), triethylamine (0.152 g, 1.50 mmol) and 1-hydroxybenzotriazole (HOBT, 0.121 g, 0.90 mmol) were sequentially added to DMF (10 ml), and the resulting mixture was stirred at room temperature for 10 h. Water (10 ml) was added to quench the reaction, and ethyl acetate (15 ml×3) was added for extraction. The organic phases were combined, and dried over anhydrous sodium sulfate. The solvent was removed, and the concentrate was separated by column (eluent: ethyl acetate/methanol (v/v)=50:1) to give 0.25 g of a white solid, with a yield of 69%. LC-MS (APCI): m/z=489.68 (M+1)⁺.

Step 2 Synthesis of Compound A-5

At 0° C., LiAlD₄ (0.043 g, 1.02 mmol) was added to a solution of compound 31 (0.25 g, 0.51 mmol) in tetrahydrofuran (10 ml), after which, the reaction was continued for 0.5 h. 1 M hydrochloric acid (10 ml) was added to quench the reaction, and the resulting mixture was extracted with ethyl acetate (20 ml×3). The organic phases were combined, dried over anhydrous sodium sulfate, and the concentrate was separated by column (eluent: ethyl acetate/methanol (v/v)=20:1) to give 65 mg of a white solid, with a yield of 27%. LC-MS (APCI): m/z=463.42 (M+1)⁺. ¹H NMR (400 MHz, DMSO) δ 12.03 (s, 1H), 8.26 (s, 1H), 8.18 (s, 1H), 7.83 (s, 1H), 7.58 (d, 1H), 7.29 (dd, 1H), 6.82 (dd, 1H), 3.80 (s, 2H).

Example 6

Preparation of 6-(4-bromo-2-chlorophenylamino)-7-fluoro-3-methyl-3H-benzimidazole-5-carboxylic acid (2-hydroxyethoxy-1,1,2,2-d₄)amide (compound A-6)

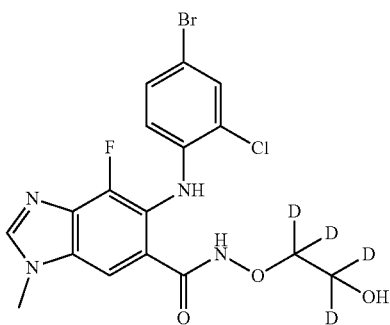

A-6

The following route was used for the synthesis:

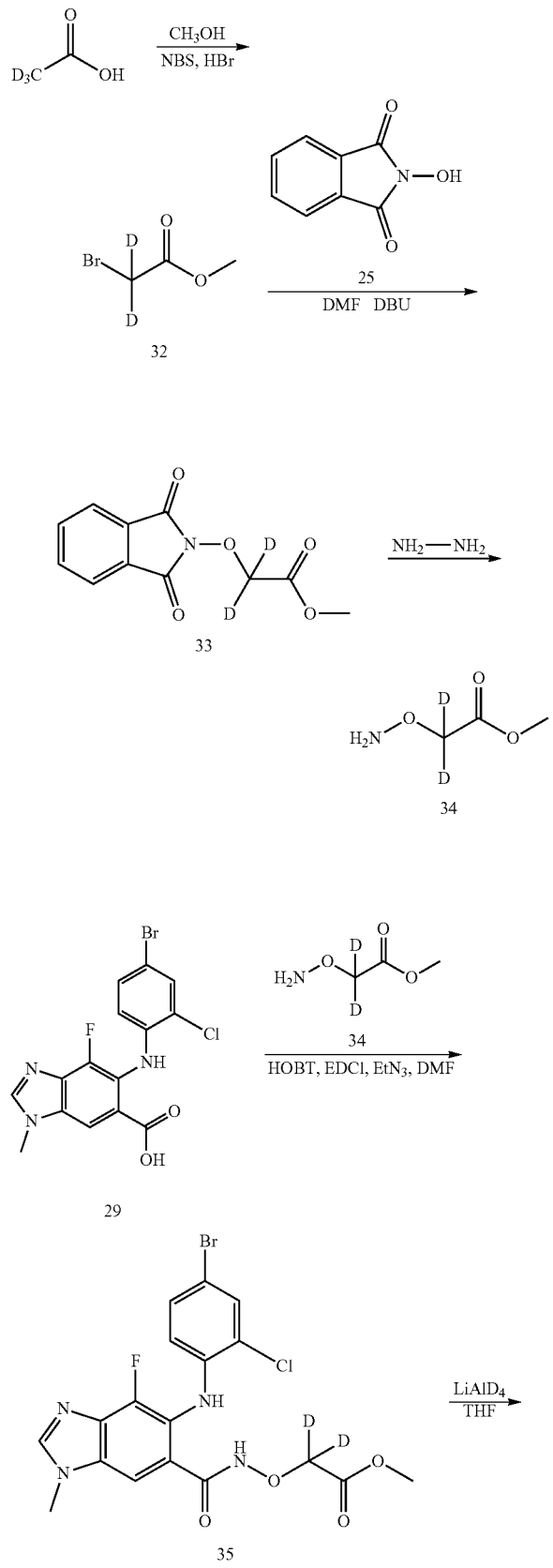

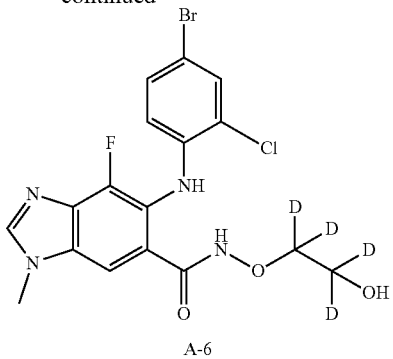

Step 1 Synthesis of Compound 32

At room temperature, DMSO (dimethyl sulfoxide, 8 ml) was slowly added to a solution of deuterated acetic acid (5.0 g, 78 mmol) in $CHCl_3$ (15 mL), and the resulting solution was heated to reflux and reacted for 1 h. After cooling to room temperature, NBS (17.0 g, 95 mmol), HBr (0.5 mL) and $CHCl_3$ (30 mL) were added, and the reaction solution was refluxed for 2 h. After cooling to room temperature, ice water (50 ml) was added to quench the reaction, and dichloromethane (50 ml×3) was added for extraction. The organic phases were combined, washed with water, washed with sodium bicarbonate solution, and dried over anhydrous sodium sulfate. The solvent was removed to give 5.2 g of a liquid product, with a yield of 42%.

Step 2 Synthesis of Compound 33

At room temperature, compound 32 (3.00 g, 20.2 mmol) was slowly added dropwise to a solution of compound 25 (3.0 g, 18.4 mmol) and 1,8-diazabicycloundec-7-ene (4.20 g, 27.6 mmol) in DMF (50 mL), after which, the reaction solution was reacted overnight. Water (50 ml) was added to quench the reaction, and the resulting mixture was extracted with ethyl acetate (50 ml×3). The organic phases were combined, washed with water, and dried over anhydrous sodium sulfate. The solvent was removed to give a white solid, and then 50 ml of 5:1 petroleum ether and ethyl acetate was added to form a slurry, which was filtered to give 2.8 g of a white solid product, with a yield of 62%.

Step 3 Synthesis of Compound 34

At room temperature, hydrazine hydrate (0.88 g, 17.7 mmol) was slowly added dropwise to a solution of compound 33 (2.8 g, 11.8 mmol) in dichloromethane (20 mL), after which, the reaction was continued for 4 h. After the filtration, the filtrate was dried with a rotary evaporator. Then n-hexane (20 ml) was added to the residue, stirring for 2 h to form a slurry. After the filtration, the filtrate was dried with a rotary evaporator to give 0.45 g of an oil product, with a yield of 35%. LC-MS (APCI): m/z=108.01 $(M+1)^+$.

Step 4 Synthesis of Compound 35

Compound 29 (0.60 g, 1.5 mmol), compound 34 (0.36 g, 3.0 mmol), 1-(3-dimethylaminopropyl)-3-ethylcarbodiimide hydrochloride (EDCI, 0.35 g, 1.8 mmol), triethylamine (0.31 g, 3.0 mmol) and 1-hydroxybenzotriazole (0.24 g, 1.8 mmol) were sequentially added to DMF (10 ml), and the resulting mixture was stirred at room temperature for 10 h. Water (10 ml) was added to quench the reaction, and ethyl acetate (15 ml×3) was added for extraction. The organic phases were combined, and dried over anhydrous sodium sulfate. The solvent was removed, and the concentrate was separated by column (eluent: ethyl acetate/methanol (v/v)= 50:1) to give 0.30 g of a white solid, with a yield of 41%. LC-MS (APCI): m/z=487.12 $(M+1)^+$.

Step 5 Synthesis of Compound A-6

At 0° C., LiAlD$_4$ (0.053 g, 1.22 mmol) was added to a solution of compound 35 (0.30 g, 0.61 mmol) in tetrahydrofuran (10 ml), after which, the reaction was continued for 0.5 h. 1 M hydrochloric acid (10 ml) was added to quench the reaction, and the resulting mixture was extracted with ethyl acetate (20 ml×3). The organic phases were combined, dried over anhydrous sodium sulfate, and the concentrate was separated by column (eluent: ethyl acetate/methanol (v/v)=20:1) to give 85 mg of a white solid, with a yield of 30%. LC-MS (APCI): m/z=461.82 (M+1)$^+$. $^1$H NMR (400 MHz, DMSO-d$_6$) δ 11.83 (s, 1H), 8.24 (s, 1H), 8.18 (s, 1H), 7.73 (s, 1H), 7.52 (d, 1H), 7.28 (dd, 1H), 6.69 (dd, 1H), 3.95 (s, 3H).

Example 7

Preparation of 6-(4-bromo-2-chlorophenylamino)-7-fluoro-3-(methyl-d$_3$)-3H-benzimidazole-5-carboxylic acid (2-hydroxyethoxy-1,1,2,2-d$_4$)amide (compound A-7)

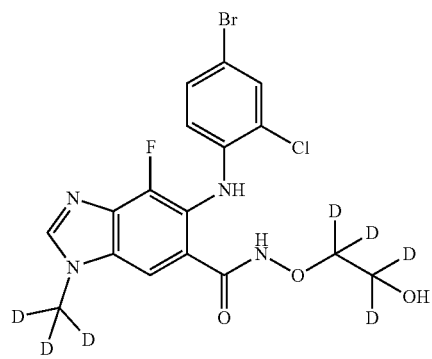

The following route was used for the synthesis:

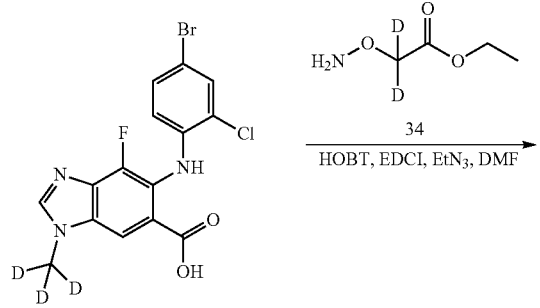

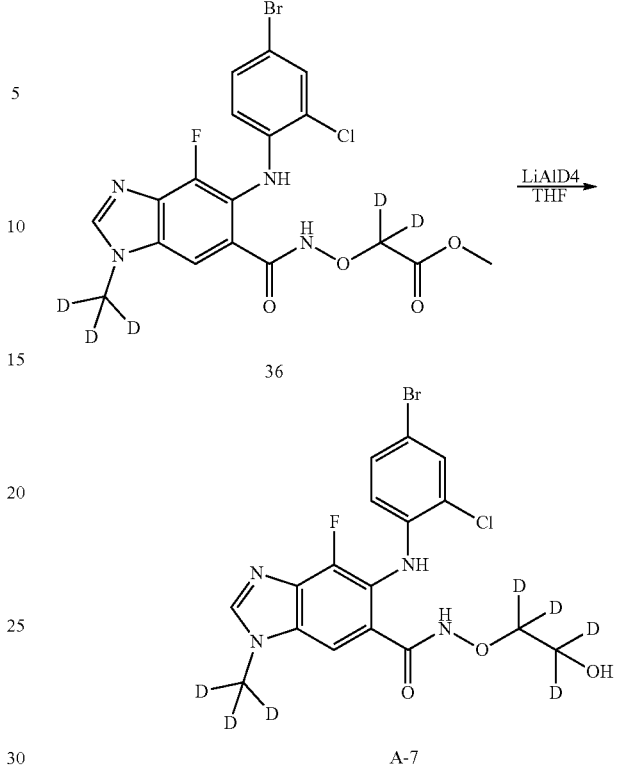

Step 1 Synthesis of Compound 36

Compound 11 (0.15 g, 0.33 mmol), compound 34 (0.045 g, 0.45 mmol), 1-(3-dimethylaminopropyl)-3-ethylcarbodiimide hydrochloride (EDCI, 0.086 g, 0.45 mmol), triethylamine (0.075 g, 0.74 mmol) and 1-hydroxybenzotriazole (0.061 g, 0.45 mmol) were sequentially added to DMF (10 ml), and the resulting mixture was stirred at room temperature for 10 h. Water (10 ml) was added to quench the reaction, and ethyl acetate (15 ml×3) was added for extraction. The organic phases were combined, and dried over anhydrous sodium sulfate. The solvent was removed, and the concentrate was separated by column (eluent: ethyl acetate/methanol (v/v)=40:1) to give 0.10 g of a white solid, with a yield of 56%. LC-MS (APCI): m/z=490.09 (M+1)$^+$.

Step 2 Synthesis of compound A-7

At 0° C., LiAlD$_4$ (0.020 g, 0.42 mmol) was added to a solution of compound 36 (0.10 g, 0.21 mmol) in tetrahydrofuran (10 ml), after which, the reaction was continued for 0.5 h. 1 M hydrochloric acid (10 ml) was added to quench the reaction, and the resulting mixture was extracted with ethyl acetate (20 ml×3). The organic phases were combined, dried over anhydrous sodium sulfate, and the concentrate was separated by column (eluent: ethyl acetate/methanol (v/v)=20:1) to give 45 mg of a white solid, with a yield of 47%. LC-MS (APCI): m/z=464.27 (M+1)$^+$. $^1$H NMR (400 MHz, DMSO-d$_6$) δ 11.85 (s, 1H), 8.39 (s, 1H), 8.22 (s, 1H), 7.83 (s, 1H), 7.56 (d, 1H), 7.33 (dd, 1H), 6.70 (dd, 1H).

Biological Activity Assay (1) Cytotoxicity Experiment

The inhibitory effects of the example compounds on the viability of HT-29 cells were tested.

Cell line: HT-29 (cell type: adherent; number of cells/well: 3000; medium: RPMI-1640+10% FBS) was cultured under the condition of 37° C., 5% CO$_2$, and 95% humidity.

Materials and Reagents: Fetal bovine serum (FBS, GBICO, Cat. No. 10099-141), CellTiter-Glo® Luminescent Cell Viability Assay (Promega, Cat. No. G7572), 96-well plate with transparent flat bottom and black walls (Corning®, Cat. No. 3603).

Instruments: SpectraMax multi-label microplate reader, MD, 2104-0010A; $CO_2$ incubator, Thermo Scientific, Model 3100 Series; biosafety cabinet, Thermo Scientific, Model 1300 Series A2; inverted microscope, Olympus, CKX41SF; refrigerator, SIEMENS, KK25E76TI.

Experimental Protocol:

1) Cell culture and inoculation: i) cells in the logarithmic growth phase were harvested and counted using a platelet counter. The cell viability was determined by trypan blue exclusion method to ensure that the cell viability was greater than 90%; ii) the cell concentration was adjusted; and 90 μL of the cell suspension was added into a 96-well plate, respectively; iii) the cells in the 96-well plate were cultured overnight under the condition of 37° C., 5% $CO_2$ and 95% humidity.

2) Drug dilution and dosing: i) the 10-fold drug solutions were prepared with a maximum concentration of 100 μM, which was diluted using a 3.16-fold serial gradient dilution, resulting in 9 concentrations. 10 μL of the drug solutions was added to each well of the 96-well plate inoculated with cells; and each drug concentration was tested in triplicate; ii) the cells in the 96-well plate added with drugs were cultured under the condition of 37° C., 5% $CO_2$ and 95% humidity for 72 hours, and then CTG analysis was carried out.

3) Plate reading at the end point: i) CTG reagent was thawed and the cell plate was equilibrated to room temperature for 30 minutes; ii) equal volume of the CTG solution was added to each well; iii) the cell plate was shaked on the orbital shaker for 5 minutes to lyse the cells; iv) the cell plate was placed at room temperature for 20 minutes to stabilize the cold light signal; v) the cold light values were read.

Data processing: GraphPad Prism 5.0 software was used to analyze the data, and the data was fitted using the non-linear S-curve regression to get a dose-effect curve, and $IC_{50}$ values were calculated accordingly. Cell viability (%)= (Lum of test drug–Lum of medium control)/(Lum of cell control–Lum of medium control)×100%.

The compounds of the present disclosure were tested in the above cytotoxicity experiment. The results show that, compared with the non-deuterated compound Selumetinib, the compounds of the present disclosure have more potent or equivalent activity on HT-29 cells. The inhibition results of the representative example compounds on in vitro proliferation of cancer cells are summarized in Table 1 below:

TABLE 1

| Example compound | HT-29 cell $IC_{50}$ (nM) |
| --- | --- |
| Selumetinib | <0.5 |
| A-1 | <0.5 |
| A-4 | <0.5 |
| A-5 | <0.5 |

(2) Metabolic Stability Evaluation

Microsome assay: mouse liver microsomes: 0.5 mg/mL, Xenotech; coenzyme (NADPH/NADH): 1 mM, Sigma Life Science; magnesium chloride: 5 mM, 100 mM phosphate buffer (pH 7.4).

Preparation of stock solutions: Powder of the example compounds were accurately weighed and dissolved in DMSO to 5 mM respectively.

Preparation of phosphate buffer (100 mM, pH7.4): A pre-prepared 0.5M potassium dihydrogen phosphate (150 mL) was mixed with 0.5M dibasic potassium phosphate (700 mL). The pH of the mixture was adjusted to 7.4 with 0.5M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-P D, 3.3 mM magnesium chloride) was prepared and placed on wet ice prior to use.

Preparation of stop solution: an acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, to which 812.5 μL of SD mouse liver microsomes were added, and mixed to obtain a liver microsome dilution with a protein concentration of 0.625 mg/mL.

Incubation of the samples: The stock solutions of the respective compounds were respectively diluted to 0.25 mM with an aqueous solution containing 70% acetonitrile, and used as a working solution, ready for use. 398 μL of the dilutions of mouse liver microsomes were added to 96-well incubation plates (N=2), respectively, and 2 μL of 0.25 mM working solution was added respectively and mixed.

Metabolic stability assay: 300 μL of pre-chilled stop solution was added to each well of 96-well deep well plates and placed on ice as stop plates. The 96-well incubation plates and NADPH regeneration system were placed in a 37° C. water bath, shaken at 100 rpm and pre-incubated for 5 min. 80 μL of incubation solution was taken out from each well of the incubation plates and added to the stop plates, mixed, and replenished with 20 μL of NADPH regeneration system solution as a 0-min sample. 80 μL of NADPH regeneration system solution was added to each well of the incubation plates to start the reaction and start counting. The corresponding compounds had a reaction concentration of 1 μM and the protein concentration was 0.5 mg/mL. Separately, 100 μL of the reaction solutions was taken at 10, 30, and 90 min after the reaction, respectively, added to stop plates, and vortexed for 3 minutes to terminate the reaction. The stop plates were centrifuged at 5000×g at 4° C. for 10 min. 100 μL of the supernatant was added to a 96-well plate to which 100 μL of distilled water was previously added, mixed, and analyzed by LC-MS/MS.

Data analysis: The peak areas of the corresponding compounds and internal standard were detected by LC-MS/MS system, and the ratio of the peak area of the compounds to the internal standard was calculated. The slope was measured by plotting the natural logarithm of the percent of remaining compound versus time, and $t_{1/2}$ and $CL_{int}$ were calculated according to the equation below, where V/M equals to 1/protein concentration.

$$t_{1/2} = -\frac{0.693}{\text{slope}}, CL_{int} = \frac{0.693}{t_{1/2}} \cdot \frac{V}{M}, t_{1/2}(\min); CL_{int}(\mu L/\min/mg).$$

The metabolic stability of the compounds in mouse liver microsomes was evaluated by simultaneously testing and comparing the compounds disclosed herein and the non-deuterated compound Selumetinib. The half-life and liver intrinsic clearance as indicators of metabolic stability are shown in Table 2. The experimental results show that: compared with the non-deuterated compound Selumetinib, the compounds of the present disclosure have significantly improved metabolic stability.

TABLE 2

| Example compound | $t_{1/2}$ (min) | CL (μL/min/mg) |
|---|---|---|
| Selumetinib | 58.7 | 23.6 |
| A-1 | 70.3 | 19.7 |
| A-4 | 56.4 | 24.6 |
| A-5 | 66.4 | 20.9 |
| A-6 | 70.2 | 19.8 |

(3) Pharmacokinetic Experiment in Rats

Six male Sprague-Dawley rats, 7 to 8 weeks old, weighted approximately 210 g, were divided into 2 groups with 3 rats in each group. The pharmacokinetic differences of the compounds were compared after they were administered to the rats at a single dose through vein or mouth (orally 10 mg/kg).

The rats were fed with standard feed and water, and fasted 16 hours before the experiment. The drugs were dissolved with PEG400 and dimethyl sulfoxide. The blood samples were collected from eyelids at the time point of 0.083, 0.25, 0.5, 1, 2, 4, 6, 8, 12 and 24 hours after administration.

The rats were anesthetized for a short time after inhaling ether, and 300 μL of blood samples was collected from the eyelids and put into test tubes, which contain 30 μL of 1% heparin salt solution. The test tubes were dried overnight at 60° C. prior to use. After the blood sample collection at the last time point, the rats were sacrificed after the ether anesthesia.

Immediately after the collection of the blood samples, the test tubes were gently inverted at least 5 times to ensure the fully mixing and placed on ice. The blood samples were centrifuged at 4° C., 5000 rpm for 5 minutes to separate the plasma from the red blood cells. 100 μL of plasma was pipetted into a clean plastic centrifuge tube, with the name of the compound and time point on it. The plasma was stored at −80° C. before analysis, and LC-MS/MS was used to determine the concentration of the compounds disclosed herein in plasma. Pharmacokinetic parameters were calculated based on the plasma concentrations of each animal at different time points.

The experiment shows that the compounds disclosed herein have better pharmacokinetic properties in animals, and therefore have better pharmacodynamics and therapeutic effects.

The above content is a further detailed description disclosed herein in combination with specific preferred embodiments, and it cannot be assumed that the specific implementation disclosed herein is limited to these descriptions. For a person of ordinary skill in the art to which the present disclosure pertains, a number of simple deductions or substitutions can be made without departing from the concept disclosed herein, and should all be considered as falling within the protection scope disclosed herein.

The invention claimed is:

1. A compound of formula (I), or a pharmaceutically acceptable salt, prodrug, hydrate, solvate, polymorph, stereoisomer or isotopic variant thereof:

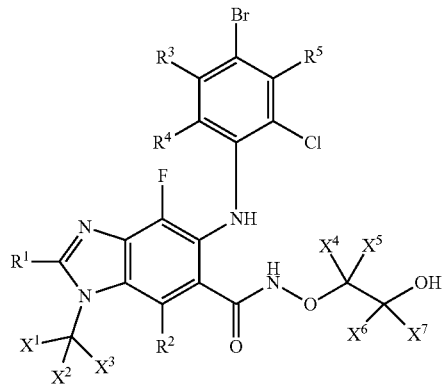

Formula (I)

wherein, $R^1$, $R^2$, $R^3$, $R^4$, $R^5$, $X^1$, $X^2$, $X^3$, $X^4$, $X^5$, $X^6$ and $X^7$ are independently selected from hydrogen and deuterium; with the proviso that at least one of $X^1$, $X^2$, and $X^3$ is deuterium.

2. The compound according to claim 1, wherein $R^1$, $R^2$, $R^3$ and $R^5$ are hydrogen.

3. The compound according to claim 1, wherein $R^4$ is hydrogen.

4. The compound according to claim 1, wherein $X^4$ and $X^5$ are hydrogen.

5. The compound according to claim 1, wherein $X^6$ and $X^7$ are hydrogen.

6. The compound according to claim 1, wherein $X^1$, $X^2$ and $X^3$ are deuterium.

7. The compound, or the pharmaceutically acceptable salt, prodrug, hydrate, solvate, polymorph, stereoisomer or isotopic variant thereof according to claim 1, wherein the compound is selected from the following compounds:

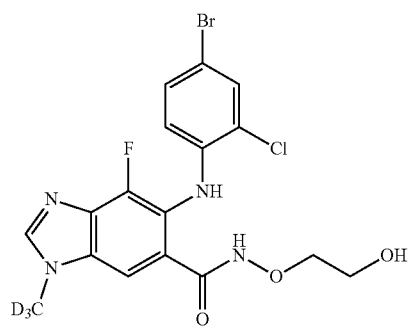

Formula (5)

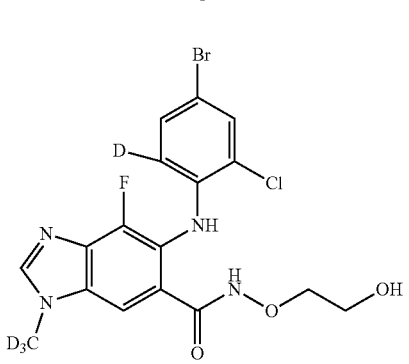

Formula (10)

Formula (11)
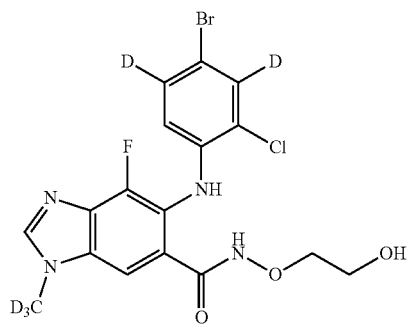
Formula (12)
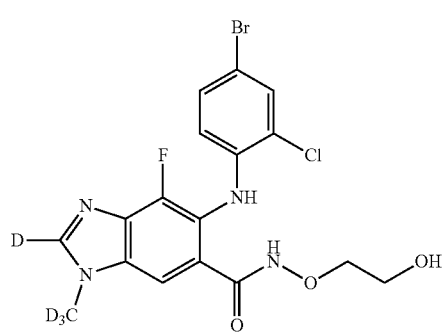
Formula (13)
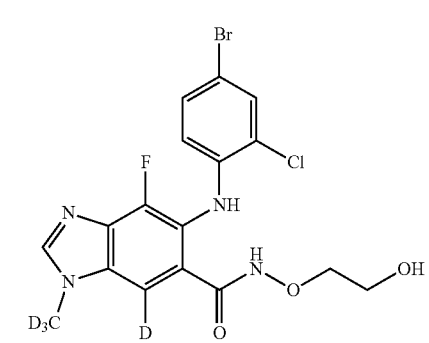
Formula (14)
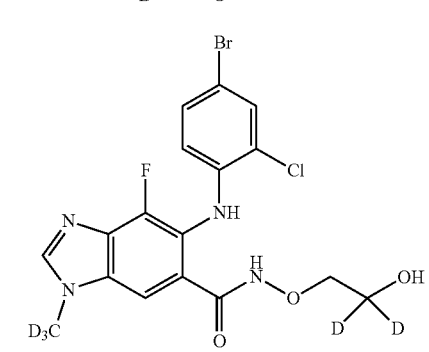
Formula (15)
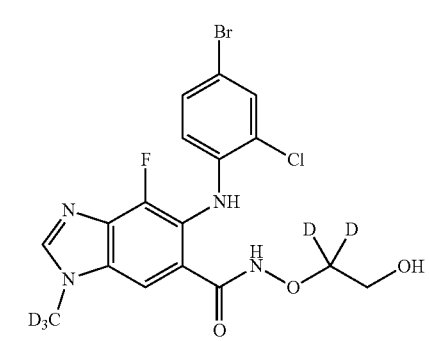
Formula (20)
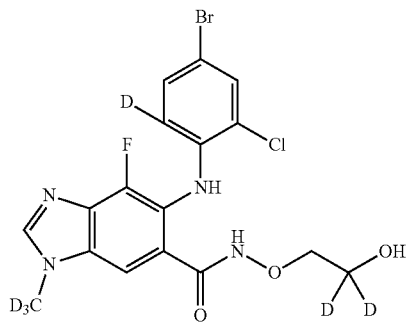
Formula (21)
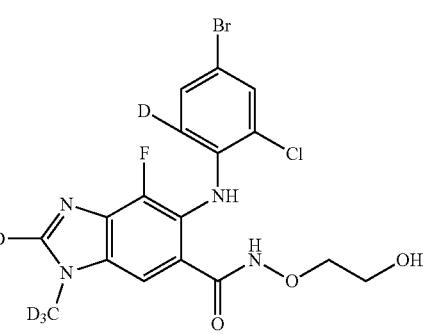
Formula (22)
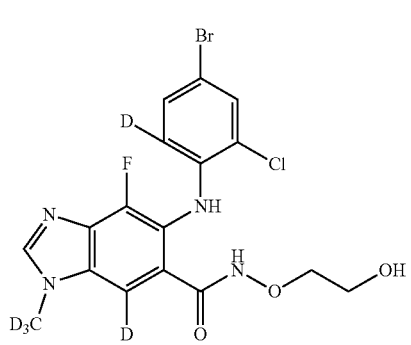
Formula (23)
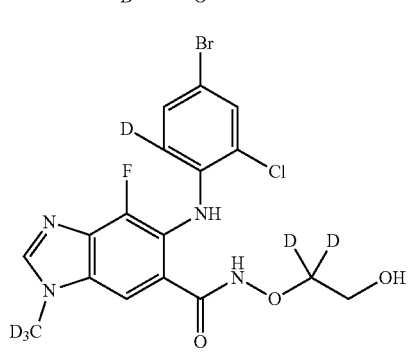
Formula (24)
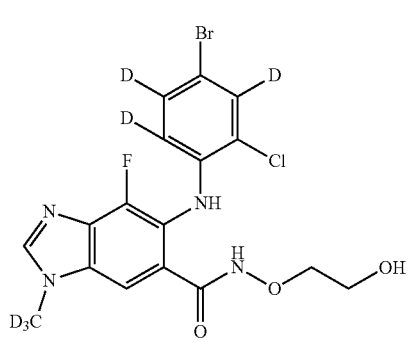

-continued

Formula (26)

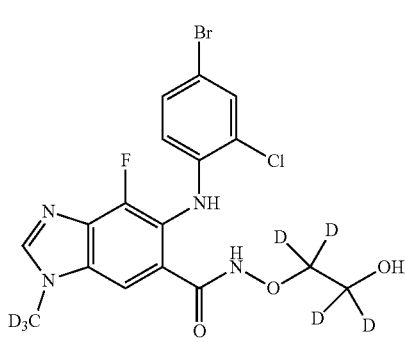

Formula (30)

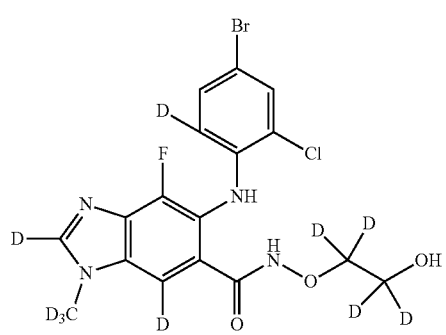

Formula (31)

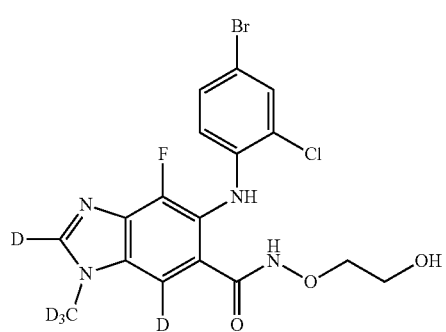

Formula (32)

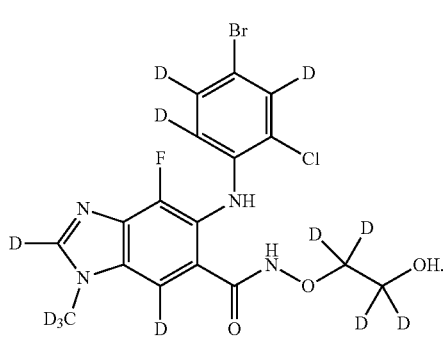

8. A pharmaceutical composition, comprising pharmaceutically acceptable excipient(s) and the compound, or the pharmaceutically acceptable salt, prodrug, hydrate, solvate, polymorph, stereoisomer or isotopic variant thereof according to claim 1.

9. A method of treating and/or preventing diseases caused by MEK in a subject, comprising administering to the subject a compound of formula (I), or the pharmaceutically acceptable salt, prodrug, hydrate, solvate, polymorph, stereoisomer or isotopic variant thereof according to claim 1.

10. The method according to claim 9, wherein the disease caused by MEK is selected from hyperproliferative disease, pancreatitis, renal disease, embryonic cell transplantation, disease related to vasculogenesis and angiogenesis.

11. The method according to claim 10, wherein the hyperproliferative disease is selected from brain cancer, lung cancer, squamous cell carcinoma, bladder cancer, gastric cancer, pancreatic cancer, breast cancer, head and neck cancer, kidney cancer, ovarian cancer, prostate cancer, colorectal cancer, esophageal cancer, testicular cancer and thyroid cancer.

12. A compound of formula (I), or a pharmaceutically acceptable salt, prodrug, hydrate, solvate, polymorph, stereoisomer or isotopic variant thereof:

Formula (I)

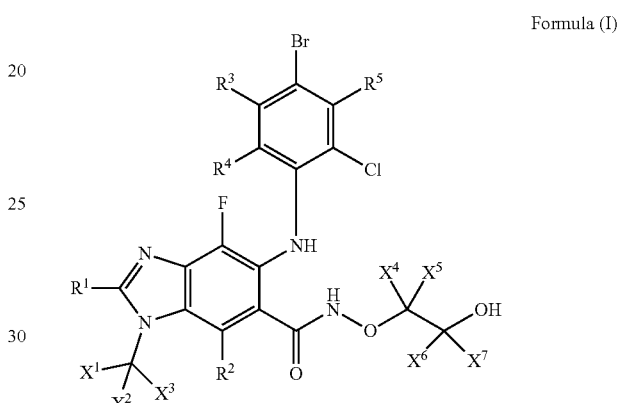

wherein, $R^1$, $R^2$, $R^3$, $R^4$, $R^5$, $X^1$, $X^2$ and $X^3$ are independently selected from hydrogen and deuterium; and $X^4$, $X^5$, $X^6$ and $X^7$ are deuterium.

13. The compound according to claim 12, wherein $R^1$, $R^2$, $R^3$ and $R^5$ are hydrogen.

14. The compound according to claim 12, wherein $R^4$ is hydrogen.

15. The compound according to claim 12, wherein $X^1$, $X^2$ and $X^3$ are deuterium.

16. The compound, or the pharmaceutically acceptable salt, prodrug, hydrate, solvate, polymorph, stereoisomer or isotopic variant thereof according to claim 12, wherein the compound is selected from the following compounds:

Formula (25)

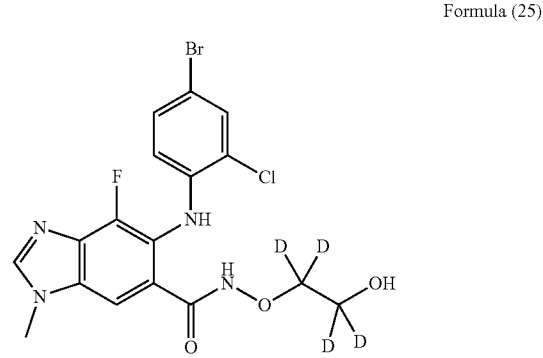

Formula (26)
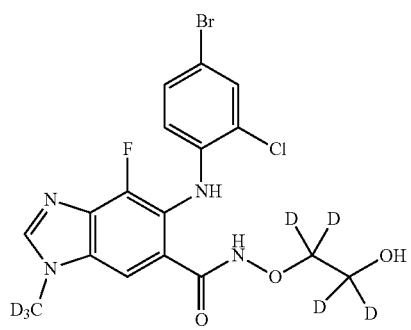
Formula (27)
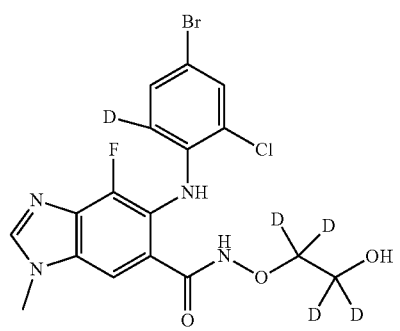
Formula (30)
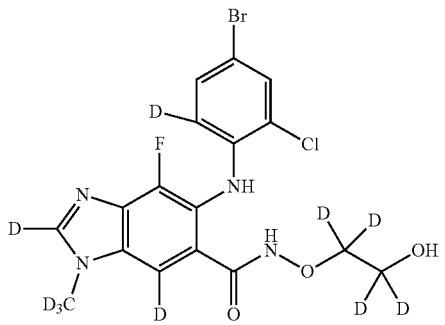
and
Formula (32)
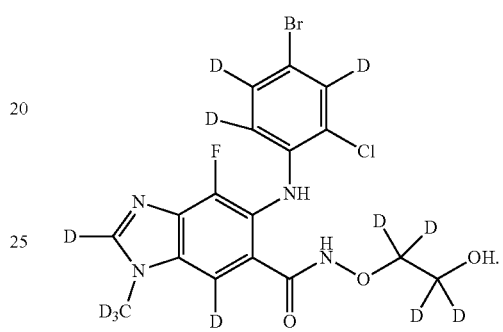
* * * * *